United States Patent [19]

Ellis et al.

[11] Patent Number: 5,573,932

[45] Date of Patent: Nov. 12, 1996

[54] OCS ELEMENT

[75] Inventors: Jeff G. Ellis, Macquarie; Daniel J. Llewellyn, O'Connor; W. James Peacock, Deakin; Elizabeth Dennis, Yarralumla, all of Australia; David Bouchez, Versaille, France

[73] Assignee: Mycogen Plant Sciences, Inc., San Diego, Calif.

[21] Appl. No.: 525,897

[22] Filed: May 18, 1990

Related U.S. Application Data

[63] Continuation-in-part of Ser. No. 11,614, Feb. 6, 1987, abandoned.

[51] Int. Cl.⁶ .......................... C12N 15/29; C12N 15/32; C12N 15/82; C12N 15/84
[52] U.S. Cl. .................. 435/172.3; 435/69.1; 435/70.1; 435/240.4; 435/252.2; 536/23.6; 536/23.71; 536/24.1
[58] Field of Search .................. 435/69.1, 70.1, 435/172.3, 240.4, 320.1, 252.2; 536/27, 24.1, 23.6, 23.71; 935/35, 36, 67

[56] References Cited

PUBLICATIONS

Bruce et al. 1988. Proc. Natl. Acad. Sci. USA 85(12):4310–4314.
Singh et al. 1989. Proc. Natl. Acad. Sci. USA 86(10):3733–3737.
Tokuhisa, J. G. et al. (1990) Cell 2:215–224.
Bouchez, D. et al. (1989) The EMBO J. 8(13):4197–4201.
Odell et al. (1985) Nature 313:810–812.
Ellis et al. (1987) EMBO J. 6:11–16.
DeGreve et al. (1983) J. Mol. App. Genet. 1:499–511.
Koncz et al. (1983) EMBO J. 2:1597–1603.
Ellis et al. (1987) EMBO J. 6:3203–3208.
Leisner et al. (1988) Proc. Natl. Acad. Sci. 85:2553–2557.
An et al. (1986) Mol. Gen. Genet. 203:245–250.
Mitra and An (1989) Mol. Gen. Genet. 215: 294–299.
Ow et al. (1987) Proc. Natl. Acad. Sci. 84: 4870–4874.
Fang et al. (1989) The Plant Cell 1:141–150.
Peacock et al. (1987) UCLA SYMP. Mol. Cell Biol., New Ser., 62:263–277, Proceedings of a Symposium Feb. 2–8, 1987.

Primary Examiner—David T. Fox
Attorney, Agent, or Firm—Saliwanchik & Saliwanchik

[57] ABSTRACT

A DNA fragment is provided which is a plant enhancer element capable of activating or enhancing the transcription level of a plant-expressible gene consisting essentially of a consensus sequence selected from the group consisting of

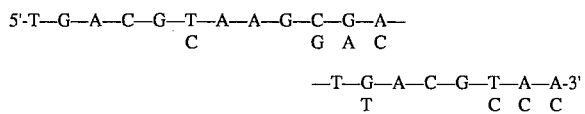

and its reverse sequence. Said DNA fragment may also contain a second sequence 5'-ACGTAAGCGCTTACGT-3'. These sequences bind with ocs transcription factor.

17 Claims, 22 Drawing Sheets

FIG. I

```
     -296         -286         -276         -266
       *            *            *            *
5'- CCGGTGCGAT  GCCCCCATCG  TAGGTGAAGG  GTGGAAATTA
    ‾‾‾‾
    HpaII

-256         -246         -236         -226
       *            *            *            *
    ATGATCCATC  TTGAGACCAC  AGGCCCACAA  CAGCTACCAG

-216         -206         -196         -186
       *            *            *            *
    TTTCCTCAAG  GGTCCACCAA  AA|ACGTAAGC  GCTTACGT|AC
                               ‾‾‾‾‾‾‾‾‾‾‾‾‾‾‾‾‾‾
                                        A

-176         -166         -156         -146
       *            *            *            *
    ATGGTCGATA  AGAAAAGGCA  ATTTGTA|GAT  GTTAACATC|C
                                   ‾‾‾‾‾‾‾‾‾‾‾‾‾‾‾
                                        B

-136         -126
       *            *
    AACGTCGCTT  TCAGGGATCC -3'
                    ‾‾‾‾‾
                    BamHI
```

FIG. 2  5'- GGATCCACGTAAGCGCTTACGTGGATCC -3'

| gene | ocs element region | distance ocs-tata | homology with ocs | reference |
|---|---|---|---|---|
| | 5' 3' | | | |
| Ti OCS | TCCACCAAAA ACGTAAGGCGCTTACGT ACATGGTCGA | 141 | 16/16 | De Greve et al. (1982) |
| CAMV 35S | ATCTCCACTG ACGTAAGGGATGACGC ACAATCCCAC | 027 | 12/16 | Franck et al. (1980) |
| FMV | AATGCGTATG ACGAACGCAGTGACGA CCACAAAGA | 014 | 10/16 | Richins et al. (1987) |
| CERV | TCTACTTTAG ACGTCATGCATGACGT TTAACATGCA | 027 | 10/16 | Hull et al. (1986) |
| Ri MAS1' | ATGTCAGGTT ACGTCATCGCTTACGC ATCGCCAAAG | 146 | 13/16 | this work |
| Ri MAS2' | CTTTGGCGAT GCGTAAGCGATGACGT AACCTGACAT | 128 | 13/16 | this work |
| Ti MAS1' | ATAAAAACTG ACTCGGATACTTACGT CACGTCTTGC | 026 | 09/16 | Velten et al. (1984) |
| Ti MAS2' | AATGCGCGTG ACGCTCGCGGGTGACGC CATTTCGCCT | 039 | 10/16 | Barker et al. (1983) |
| Ti NOS | GAGTTTAATG AGCTAAGCACATACGT CAGAAACCAT | 085 | 12/16 | Depicker et al. (1982) |
| Ti AGS | ATTAATCATG ACGCATCGAATGACGC GAGTGTCATT | 097 | 08/16 | Barker et al. (1983) |

CONSENSUS
```
           TG ACGTAAGGCGATGACGT AA
              C    GAC  T   C   CC
                T  CGA  G    TAA
           TGACG  AAG  T ACG
              C    GAC  T
                                 CCC
```

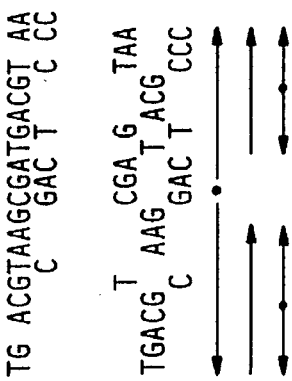

FIG. 4

```
OCS              AAACGTAAGCGCTTACGTAC
                 |||||||  |  | |||  ||
CaMV 35S    GATATCTCCACTGACGTAAGGGATGACGCACAATCCCA
MUT 1       GATATCTCCACTGACGCCTCGGATGACGCACAATCCCA          GUS ACTIVITY
MUT 2       GATATCTCCACTGTATTAAGGGATGACGCACAATCCCA
MUT 3       GATATCTCCACGAACGTAAGGGATGACGCACAATCCCA
                       ↑                     ↑
                     EcoRV                 FokI
```

FIG. 5a

```
                    XbaI              Pst I
o1IMAS    E/S/K/Sm/B/TCTAGACGTCATCGCTTACGCTGCAG/Sp/H
```

FIG. 6a oliEB
```
       EcoRI                    BamHI
       GAATTCACGTAAGCGCTTACGTGGATCC/X/Sa/P/Sp/H
``` oliAGS
```
       EcoRI                       BamHI
       GAATTCTGACGCATCGAATGACGCGGATCC/X/Sa/P/Sp/H
```

FIG. 8a

```
pNOS-SH50   E/S/K/CCCGGG TTTCTGGAGTTTAATGAGCTAAGCACATACGTCAGAAACCATTATTGCGGACCTGCAG/Sp/H
                  SmaI                                                    PstI pNOS-xP21   E/S/K/Sm/GGATCCTCTAGCTAAGCACATACGTCAGAAACCATTATTGCGGACCTGCAG/Sp/H
                     BamHI                                         PstI pNOS-KP11   GAATTCTAAGCACATACGTCAGAAACCATTATTGCGGACCTGCAG/Sp/H
            EcoRI                                   PstI pNOS-oli3   E/S/K/Sm/B/TCTAGAGCTAAGCACATACGTCACTGCAG/Sp/H
                       XbaI                   PstI pNOS-oli4   E/S/K/Sm/B/TCTAGTGAGCTAAGCACATACGTCACTGCAG/Sp/H
                                                PstI pNOS16      H/Sp/P/Sa/X/GGATCCAGCTAAGCACATACGTGAATTC
                        BamHI                 EcoRI
```

5' CTTAAGCAAGGGCTTACGTCTGCA 3'
    1 2 3 4 5 6 7 8 9 10 11 12 13 14 15 16 17 18 19 20 21 22 23 24
    GAATTCGTTCCCGAATGCAGACGT

LOWER BAND

LOWER BAND

FIG.13C

OCS ELEMENT

This application is a continuation-in-part of U.S. patent application Ser. No. 011,614, filed Feb. 6, 1987, now abandoned, incorporated herein by reference.

FIELD OF THE INVENTION

This invention is in the field of plant molecular biology and relates to plant genetic engineering by recombinant DNA technology.

BACKGROUND OF THE INVENTION

In eukaryotic genes there is a growing understanding of the DNA sequence elements which direct the initiation of transcription and which regulate or modulate gene expression. The following discussion applies to genes transcribed by RNA polymerase II. Promoters are the portions of DNA sequence at the beginnings of genes which contain the signals for RNA polymerase to begin transcription so that protein synthesis can then proceed. Eukaryotic promoters are complex, and are comprised of components which include a TATA box consensus sequence in the vicinity of about −30, and often a CAAT box consensus sequence at about −75 bp 5' relative to the transcription start site, or cap site, which is defined as +1 (R. Breathnach and P. Chambon (1981) *Ann. Rev. Biochem.* 50:349–383; J. Messing et al. (1983) in *Genetic Engineering of Plants,* T. Kosuge et al. (eds.), pp. 211–227). In plants there may be substituted for the CAAT box a consensus sequence which Messing et al. (1983) have termed the AGGA box, positioned a similar distance from the cap site. Additional DNA sequences in the 5' untranscribed region are believed to be involved in the modulation of gene expression. There are DNA sequences which affect gene expression in response to environmental stimuli, such as illumination or nutrient availability or adverse conditions including heat shock, anaerobiosis, or the presence of heavy metals. There are also DNA sequences which control gene expression during development, or in a tissue-specific fashion. Other DNA sequences have been found to elevate the overall level of expression of the nearby genes; such sequences have been termed "enhancers" in animal systems. In yeast, similar stimulatory sequences are known which are called "upstream activating sequences," which also often appear to carry regulatory information. Promoters are usually positioned 5', or upstream, relative to the start of the coding region of the corresponding gene, and the tract containing all the ancillary elements affecting regulation or absolute levels of transcription may be comprised of less than 100 bp or as much as 1 kbp.

As defined by Khoury and Gruss (1983) *Cell* 33:313–314, an enhancer is one of a set of eukaryotic promoter elements that appears to increase transcriptional efficiency in a manner relatively independent of position and orientation with respect to the nearby gene. The prototype enhancer is found within the 72 bp repeat of SV40. It is located more than 100 bp upstream from the transcription start site, and has a consensus core sequence of GTGGAAA(or TTT)G. As a rule the animal or animal virus enhancers can act over a distance as much as 1 kbp 5', in either orientation, and can act either 5' or 3' to the gene. The sequence motif is generally reiterated several times. Enhancers have been used in animal virus systems to study genes with weak promoters (F. Lee et al. (1981) *Nature* 294:228–232; A. Huang et al. (1981) *Cell* 27:245–255). There have been sequences from plant genes described which have homology to the animal enhancer consensus core sequence. A functional role for these sequences has not been established. One example in which such homology has been found is that of the pea legumin gene 5' region in which the sequence 5'-CCACCTCC-3' appears at about −180 relative to the transcription start site. This sequence shows about 80% homology to the complement of the animal sequence (G. Lycett et al. (1984) *Nucleic Acids Res.* 12:4493–4506). Two other examples where a similar sequence appears are in the 5'-flanking regions of the maize adh1 and adh2 genes. In those cases the sequence of note is CACCTCC, and appears at about −170 for adh2 and −200 for adh1 (E. Dennis et al. (1985) *Nucleic Acids Res.* 13:727–743; and D. Llewellyn et al. (1985) in *Molecular Form and Function of the Plant Genome,* van Vloten-Doting et al. (eds.), Plenum Press, New York).

The yeast upstream activating sequences (UAS) have somewhat different properties than those of the animal enhancers. Like the animal enhancers the yeast UAS's function when inserted in either orientation; they do not appear able to activate transcription when placed 3' to the transcription start site (L. Guarente and E. Hoar (1984) *Proc. Natl. Acad. Sci. USA* 81:7860–7864; and K. Struhl (1984) *Proc. Natl. Acad. Sci. USA* 81:7865–7869). Sequences of the activating regions of some yeast promoter elements are known, and in at least two cases, homology to the SV40 enhancer consensus core sequence has been shown (B. Errede et al. (1985) *Proc. Natl. Acad. Sci. USA* 82:5423–5427, and G. Roeder et al. (1985) *Proc. Natl. Acad. Sci. USA* 82:5428–5432). Associated with these sequences is also information allowing the cell to respond to stimuli such as nutritional status or mating type, depending on the particular UAS.

Another case where upstream sequence motifs regulate downstream transcriptional activity is that of the heat shock element. It is involved with the control of genes expressed in response to the stress of elevated temperature in organisms from yeast to man and plants. In Drosophila the consensus sequence for the motif is 5'-CTGGAAT-TTCTAGA-3' (H. Pelham and M. Bienz (1982) in *Heat Shock From Bacteria to Man,* Cold Spring Harbor Laboratory, pages 43–48). D. Rochester et al. (1986) *EMBO J.* 5:451–458, have identified two sequences 5' to the maize hsp70 heat shock gene which are partially homologous to the consensus sequences: 5'- CCAGAGCCTTCCAGAA-3' and 5'-CCCGAATCTTCTGGA-3'.

Recently there has been a surge of interest in plant control elements; there have been sequences proposed to be involved in tissue specificity and in responses to light and anaerobic conditions, and there have been postulated enhancer-like sequences 5' to (some) highly expressed genes. One report of an enhancer-like sequence is that of J. Odell et. al. (1985) *Nature* 313:810–812, who have described the stretch of 5' nontranscribed region of the 35S gene of Cauliflower Mosaic Virus (CaMV) which is necessary for promoting the expression of a reporter gene. Examination of the sequence in the −105 to −46 region revealed a CAAT box-like sequence, an inverted repeat region, and a sequence resembling the animal core sequence for enhancers. It has been demonstrated (Ellis et al. (1987) *EMBO J.* 6:11–16) that a 309 bp fragment (−395 to −86) from the region 5' of the TATA box of the 35S promoter is responsible for enhancing transcriptional activity. It is known that although the host range of the CaMV is limited to members of the family Cruciferae, the entire 35S promoter does function in tobacco (J. Odell et al. (1985) supra, M. Bevan et al. (1985) *EMBO J. 4:1921–1926*).

Literature concerning cross expression studies, wherein a gene from one plant species is examined for expression in a different species, is growing. An early report of cross expression is that of N. Murai et al. (1983) *Science* 222:476–482. They reported the expression of phaseolin protein from *Phaseolus vulgaris* L. in sunflower (Helianthus) tissue as both a fusion protein behind a T-DNA promoter and under the control of its own promoter. Sengupta-Gopalan et al. subsequently reported that the phaseolin promoter and structural gene were functional in tobacco, and that the tissue-specific expression in the heterologous host was similar to that in the native bean host (C. Sengupta-Gopalan et al. (1985) *Proc. Natl. Acad. Sci. USA* 82:3320–3324).

W. Gurley et al. (1986) *Mol. Cell Biol.* 6:559–565 described the expression of a soybean heat shock gene in sunflower tumor tissue; the gene was strongly transcribed, and with the correct thermal induction response. Because the gene carried 3.2 kb of upstream DNA, it was presumably transcribed in response to signals carried by its own promoter.

Another example is that of J. Jones et al. (1985) *EMBO J.* 4:2411–2418. The promoter from a petunia chlorophyll a/b binding protein gene was fused to the octopine synthase gene (ocs), which provided unique sequence for detection in Northern and solution hybridization experiments. These workers found that transcription occurred in both regenerated transformed homologous (petunia) and heterologous (tobacco) plants. Ocs reporter gene activity was not detected, perhaps because the construction yielded a (potential) translational fusion with three amino acid substitutions at the amino terminus of the Ocs polypeptide.

A report of expression across the monocot-dicot boundary is that of G. Lamppa et al. (1985) *Nature* 316:750–752. The wheat gene whAB1.6 encoding the major chlorophyll a/b binding protein was cloned into a T-DNA-containing vector, and transferred to both petunia and tobacco. Expression, at the level of transcription, was determined to be light-inducible and tissue-specific in the dicotyledonous hosts, as it was in the wheat. No data concerning the synthesis of the actual foreign protein were given.

D. Rochester et al. (1986) *EMBO J.* 5:451–458, have also detected the expression of a maize promoter in a dicotyledonous plant. The maize promoter used was that of a hybrid hsp70 gene. Hsp70 is one of a set of proteins induced in maize, as in organisms from bacteria to man, in response to heat shock. In the transgenic petunia the maize hsp70 mRNA was synthesized only in response to thermal stress.

An early study of actual plant regulatory sequences is that of M. Timko et al. (1985) *Nature* 318:579–582. A stretch of DNA from −973 to −90 5' to the transcriptional start site of the pea rbcS ss3.6 (ribulose 1,5 bis-phosphate carboxylase small subunit) was found to increase the level of induction of a reporter gene after illumination of transgenic tobacco plants. The stimulatory effect was observed when the −973 to −90 segment was inserted in both orientations; it did not promote high levels of gene expression when inserted 3' to the reporter gene. J. Simpson et al. (1985) *EMBO J.* 4:2723–2729, studied the effect of upstream sequences from the pea chlorophyll a/b binding protein AB80 gene using an enzymatic reporter. They found that 400 bp of upstream sequence carried the necessary information for both light-induction and tissue specificity, and that sequences further upstream were involved in determining the absolute level of gene expression. In a figure showing sequence data, there is a 6 bp motif highlighted as being somewhat homologous to the animal enhancer core consensus sequence, TGGATA, which occurs at about −230 relative to the start of transcription. In neither report is there definitive data associating a specific nucleotide sequence with functional activity.

In H. Kaulen et al. (1986) *EMBO J.* 5:1–8, the light induction of chalcone synthase was studied using fusions of the nontranscribed region 5' to the gene with a reporter gene. 1.2 kbp of 5' DNA gave light inducibility and maximal expression, and deletion of the −1200 to −357 gave lower expression, but the light induction response was not reported. These authors examined the sequence and found 47 bp repeats in the region between −661 and −564; that region includes a good match to the animal enhancer consensus core sequence 5'-GTGGTTAG-3'.

In recent studies published after the priority date hereof, by Schulze-Lefert et al. (1989) *EMBO J.* 8:652–656, three regions of sequence within the parsley chalcone synthase promoter were highlighted: (1) region I at around −140 is centered on the twice reiterated sequence 5'-AACCT-3'; (2) region II contains an octamer with perfect dyad symmetry (5'-CCACGTGG-3') at position—165; while (3) region III is a degenerate repeat of region II at position −230. It was shown that a chalcone synthase promoter fragment spanning from −100 to −226, containing footprint regions I and II, is light responsive in conjunction with the cognate promoter up to −100. However, sequences further 5', which include region III, clearly increase both induced and uninduced levels of glucuronidase (GUS) expression. Significantly, deletion of all three footprinted regions, leaving 100 bp of promoter, results in uninducible basal levels of GUS activity. Mutations within either region I or region II abolish inducibility, indicating that both regions I and II are necessary for a light response in the context of the minimal parsley chalcone synthase promoter.

There was a relatively thorough discussion of cis-active sequence involvement in light induction and tissue specificity in R. Fluhr et al. (1986) *Science* 232:1106–1112. They showed that the −1059 to −2 region 5' to the pea rbcS-E9 gene gave both light inducible and tissue specific expression, and that the −352 to −2 region conferred normal expression in transgenic petunias but significantly lower levels of expression in calli. The light response was elicited only when the −37 to −2 region of 5' DNA was present. The 5' −410 to +15 region from the related rbcS-3A gene gave tissue specificity and light induction. In an attempt to further dissect sequence functions, they fused the −327 to −48 fragment to an enhancerless CaMV 35S promoter-reporter gene system; that fragment gave light induction and tissue specificity when inserted in both orientations. The −317 to −82 fragment from the rbcS-E9 gave similar results. Again, sequence analysis revealed regions similar to SV40 enhancers. The authors claim that these upstream stretches of DNA have the properties of light-inducible transcription enhancers; specific DNA sequences within those regions were not identified. The authors went on to discuss the analysis of seven sequenced rbcS upstream regions in which sequences similar to the SV40 enhancer core consensus and to the yeast Ty enhancer were found. These sequenced genes included representatives from Nicotiana and soybean as well as the pea. G. Morelli et al. (1985) *Nature* 315:200–204, reported a control sequence for dicot light-regulated genes, which is 5'-CATTATATATAGC(orA)-3'. It is thought (Green et al. (1987) *EMBO J.* 6:2543–2549) that cis-acting elements function by binding to trans-acting protein factors present in plant cell nuclei. Such factors would then interact directly or via other proteins with RNA polymerase II to modulate transcription. In later studies Green et al. (1988) *EMBO J.* 7:4035–4044 defined a core of six residues (GGTTAA) within region II sequence (GTGTGGTTAATATG) that are critical for binding.

Two *Agrobacterium tumefaciens* T-DNA genes have been well characterized. The ocs gene encodes octopine synthase, and is carried on octopine-type Ti plasmids such as pTiAch5 and pti15559. The gene for nopaline synthase is nos, and it resides on the nopaline-type Ti plasmids. Both ocs and nos and their 5'-flanking regions have been sequenced (H. DeGreve et al. (1982) *J. Mol. Appl. Genet.* 1:499–511; M. Bevan et al. (1983) *Nucleic Acids Res.* 11:369–385; A. Depicker et al. (1982) *J. Mol. Appl. Genet.* 1:561–573). Expression of both of these genes in plant tissue is constitutive, and there does not appear to be tissue specificity (L. Otten et al. (1981) *Mol. Gen. Genet.* 183:209–213). However, it has recently been observed that the activity of the nos promoter is organ specific and developmentally regulated (An et al. (1988) *Plant Physiol.* 88:547–552).

There were no published data for enhancer-like activity in T-DNA 5' untranscribed regions before 1987. C. Koncz et al. (1983) *EMBO J.* 2:1597–1603, did show that the region between −294 and −170 was required for full expression of ocs. The sequence for ocs was published by H. DeGreve et al. (1983) supra, after animal and animal virus enhancers were known. The authors noted the presence of a TATA box-like sequence and a polyadenylation signal at the 3' side of the gene, but did not note any sequence of potential regulatory significance. They suggested that because the ocs promoter is close to the edge of the T-DNA, there might be flanking plant sequences that influence the levels of ocs transcription. Ellis et al. (1987) *EMBO J.* 6:3203–3208 and Leisner et al. (1988) *Proc. Natl. Acad. Sci.* 85:2553–2557 reported a 176 bp element isolated from the ocs gene which exhibited enhancer-like properties in transgenic tobacco plants. The ocs gene was transferred and integrated with the T-DNA of Agrobacterium into the genome of plant cells during initiation of the crown gall tumor. The gene was not expressed in Agrobacterium but was expressed in the plant (Otten et al. (1981) *Mol. Gen. Genet.* 183:209–213). Although the infectivity of Agrobacterium is limited generally to dicotyledonous plants, the transcriptional enhancer of the ocs promoter functions in both monocots and dicots and does not require any factors supplied by other genes of the bacterium (Hooykaas-van Slogteren et al. 1984.

There are several techniques available for introducing recombinant DNA into plant tissue for either stable integration into the plant genome or for measuring engineered gene activity in transient expression systems where incorporation into the genome is not required. Representative bacteria-to-plant T-DNA dependent cloning vector systems are described in G. An (1986) *Plant Physiol.* 81:86–91; G. An et al. (1985) *EMBO J.* 4:277–284; L. Herrera-Estrella et al. (1983) *EMBO J.* 2:987–995; L. Herrera-Estrella et al. (1983) *Nature* 303:209–213; and L. Herrera-Estrella et al. (1985) in *Plant Genetic Engineering*, J. H. Dodds (ed.), New York: Cambridge University Press, pp. 63–93. The T-DNA vectors rely on mobilization from bacteria to plant using functions supplied in trans by *Agrobacterium tumefaciens* and its resident Ti plasmid. T-DNA mediated transfer generally is effected in such a way that stable integration into the genome results. The most widely used plant host models for recombinant T-DNA work are the dicots sunflower, petunia, and tobacco. The technique of agroinfection has extended the range of monocots into which T-DNA-containing vectors can be introduced (N. Grimsley et al. (1986) *Proc. Nat. Acad. Sci. USA* 83:3282–3286).

Alternatives to the Agrobacterium-mediated DNA transfer systems are known, and include electroporation of both monocots and dicot plant protoplasts to incorporate DNA (M. Fromm et al. (1985) *Proc. Natl. Acad. Sci. USA* 82:5824–5828) and direct transformation of protoplasts with DNA molecules mediated by polyethylene glycol (J. Paszkowski et al. (1984) *EMBO J.* 3:2717–2722) or calcium ions. Another T-DNA independent means for introducing recombinant DNA is microinjection of DNA into plant cell nuclei (A. Crossway et al. (1986) *Mol. Gen. Genet.* 202:179–185). The techniques use plant cell protoplasts (wall-less forms) as the initial DNA recipients; known manipulations of protoplasts can result in cell or tissue culture, or ultimately in regenerated transformed plants. Use of such alternatives significantly expands the range of plants into which heterologous genes can be introduced. Paszkowski et al. (supra) have shown that integration into the genome is possible without the presence of T-DNA sequences.

SUMMARY OF THE INVENTION

This invention describes the identification and characterization of the octopine synthase (OCS) element, a sequence of DNA from the upstream nontranscribed region of plant-expressible genes (seven T-DNA genes involved in opine synthesis and three plant viral promoters). This nucleotide sequence is capable of activating or increasing the transcription of nearby, preferably downstream plant-expressible genes in recombinant DNA-containing tissue from both monocotyledonous and dicotyledonous plants. The OCS element is useful for increasing the level of expression of a nearby gene in a plant, especially when that gene and its associated promoter are derived from heterologous plant species. Thus, the invention will facilitate the genetic engineering of plants to express novel phenotypes of economic or investigative value. The homologous sequences were identified in the promoter regions of ocs and six other T-DNA opine synthase genes from Ti and Ri plasmids and three plant viral promoters including the promoters of the cauliflower mosaic virus (CaMV), figwort mosaic virus (FMV) and carnation etched ring virus (CERV). A twenty base pair consensus sequence,

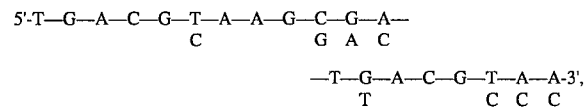

was derived by comparison of the ten promoter sequences. The name OCS element is given to members of this class of elements having similar sequence and function. These elements bind the ocs transcription factor in vitro and enhance or activate gene transcription in plant cells. The reverse of the consensus ocs sequence is also effective and is also termed an identifying sequence herein. Sequences with about 50% or greater homology, and more preferably about 75% or greater homology, to the consensus sequences can also function as plant transcription activating elements.

One effective embodiment of said consensus sequence comprises the 16 bp palindrome sequence from the 5'-untranscribed region of the octopine synthase (ocs) gene to T-DNA, 5'-ACGTAAGCGCTTACGT-3' or it reverse sequence. The consensus sequence has been found associated with other plant-expressible genes, including several T-DNA genes (see FIG. 4), and serves to enhance expression thereof.

Recombinant DNA molecules including the plant enhancer element in combination with promoter sequences heterologous thereto and structural genes under the control of the enhancer element and promoter are also provided which are useful to obtain enhanced expression in plants of such genes. The term "enhanced expression" can mean that the gene is activated when the enhancer element is present and not without it, or it can mean gene expression is increased by the enhancer. The enhancer element is useful, among other things, for activating anaerobically regulated genes, e.g., an adh gene such as maize adh1, in systems where they are not expressed without this element.

Any promoter capable of regulating expression of genes in plants may be used in this invention; preferably the promoter is not found naturally associated with the enhancer. However, if the enhancer is found naturally associated with the promoter still constructs providing repeats of said enhancer or alterations in the position of said enhancer with respect to said promoter which provide enhanced gene expression are contemplated as embodiments of this invention. Enhanced gene expression may be assayed by means well-known to the art and as taught herein.

Methods of obtaining enhanced gene expression of a plant-expressible structural gene in a transformable plant cell, plant tissue or regenerable plant are also provided comprising inserting the plant enhancer element of this invention into the genome of said plant cell such that said plant expressible structural gene is under regulatory control of said plant enhancer element and a promoter heterologous to said enhancer element in said plant cell.

The initial subject of this patent application was the identification of a nucleotide sequence 5'-ACG-TAAGCGCTTACGT-3' derived from the 5'-untranscribed flanking region of the ocs gene of T-DNA from *Agrobacterium tumefaciens* which activates the expression of a downstream gene driven by a plant-expressible promoter. This sequence has been termed a primary component of a plant enhancer element. The plant enhancer element may consist only of this component or may be a larger DNA molecule containing it, its reverse sequence, and/or repeats thereof, and may also comprise a second component described below. This functional primary component with enhancer-like activity in plants does not share sequence homology with the core consensus sequence of the prototype animal enhancer. Recombinant DNA constructs have been engineered with either a synthetic oligonucleotide comprising the aforementioned sequence or with the appropriate fragment of the ocs upstream region placed 5' to the maize anaerobically-regulated alcohol dehydrogenase (adh1) promoter with a bacterial chloramphenicol acetyl transferase (cat) reporter gene; in both instances anaerobic induction of cat enzyme activity was obtained in transformed tobacco plants. Analogous constructions without the transcriptional activating element did not give detectable expression in tobacco when either cat or adh1 served as the reporter gene. The functionality of the enhancer element was also determined using transient expression assays in cultured maize cells, and in cultured *Nicotiana plumbaginafolia* cells. Thus, the ability of the transcription activating element to function in both monocotyledonous and dicotyledonous plants has been established.

Sequences homologous to the 16 bp palindromic OCS enhancer element were identified in nine other plant expressible genes. Comparison of the ten plant promoter identifying sequences led to the formulation of a 20 bp consensus sequence, named OCS element. Different species of OCS element were shown to bind in vitro the ocs transcription factors from tobacco or maize nuclear extracts and also enhance transcription in plant cells.

The enhancer sequences of this invention can be used within or as derived from their natural source. Alternatively, the enhancer sequence can be generated using known technology for chemical synthesis of DNA oligonucleotides.

The plant enhancer element controls the level of transcription of a plant-expressible structural gene comprising a structural gene and promoter elements including a TATA box. It is preferably placed upstream of the transcription start site of a plant expressible gene anywhere from immediately 5' to the TATA box of the gene promoter (e.g., about −40 bp) to about 1500 bp 5' of the transcription start site. Ideally the enhancer element should be located between about 100 and about 300 bp 5' to the transcription start site such that the level of expression of the structural gene under the control of the promoter is increased by the presence of the enhancer element. It is preferred that the enhancer element be placed upstream of the gene it is to regulate, but it may also be placed downstream thereof where it is effective to a lesser degree.

Also found in the natural source of the primary enhancer element or OCS element is a second component, with the identifying sequence 5'-GATGTTAACATC-3'. The reverse of this sequence is also effective and is also termed an identifying sequence herein. Sequences with about 50% or greater homology, and more preferably 75% or greater homology to the identifying sequence, function in a similar manner. This second component is not required for plant transcription activation, but can contribute to the level of enhancement of downstream gene expression.

The second optional component to the enhancer element preferably is placed within about 500 bp of the primary component of the enhancer element described above, ideally within about 20 to about 100 bp of said primary component, and is effective both in the given orientation and in reverse orientation. The second component can be placed either 5' or 3' to the primary component, and in the given orientations, the second component is preferably 3' to the primary component.

The enhancer element consisting of both components is effective in reverse orientation as well as in its naturally occurring orientation with the primary component 5' to the second component. The enhancer elements function in monocotyledonous as well as in dicotyledonous plants.

Recombinant DNA molecules of this invention preferably comprise a plant enhancer element, a plant-expressible promoter, and a plant-expressible structural gene, wherein the structural gene is placed under the regulatory control of the enhancer element and the promoter. The structural gene and promoter may be from heterologous sources as long as the structural gene can be expressed in a desired plant under the control of the promoter. In most applications the enhancer element would be employed to regulate expression of a structural gene not normally (i.e., naturally) under its control.

In the method for increasing the level of expression of a plant-expressible gene in plant tissue, it is preferred that the promoters and structural genes are derived from sources other than that plant tissue in which expression is being sought.

BRIEF DESCRIPTION OF THE FIGURES

FIG. 1 gives the DNA sequence of the 176 bp fragment from the 5' untranslated region of the octopine synthase gene of the T-DNA from *Agrobacterium tumefaciens*. The 16 bp sequence with which the primary component of the plant-active transcription activating element is identified is underlined and labelled A. The 12 bp sequence which identifies the second component of the transcription activating element is underlined and labelled B.

FIG. 2 displays the DNA sequence of the oligonucleotide carrying the primary component of the plant-active transcription activating element.

FIG. 4. Sequences homologous to the ocs 16 bp palindrome (top line) found in viral genes or in opine synthase genes of TDNAs from Ti and Ri plasmids. The Ri MAS1' and Ri MAS2' are the same sequence in reverse orientations. A consensus sequence (bottom) has been derived from this alignment. The distances in base pairs of these sequence elements from their respective TATA boxes are indicated and their homologies with the ocs palindrome tabulated.

FIGS. 5a–5d. The CaMV 35S OCS element. (a) sequences of the 35S OCS element and the three mutant sequences obtained by oligonucleotide directed mutagenesis showing the homology to the ocs palindrome, the location of the restriction sites used for isolating the gel retardation probes and the sequence alterations (underlined) in the mutants. The activity of a GUS reporter gene linked to the different promoters is indicated and is the average of three experiments. (b) gel retardation obtained with the 31 bp EcoRV-FokI fragment of the wild-type 35S promoter. A strong upper band and a faint lower band were observed under the binding conditions used. Lane 1, no competitor DNA; lane 2, 48 bp competitor fragment from the ocs promoter; lane 3, competitor fragment from a cloned synthetic 16 bp ocs palindrome; lane 4, pUC polylinker as competitor. (c) a labelled DNA fragment containing a cloned ocs palindrome was used as probe. No competitor DNA (lane 1), pUC polylinker (lane 2), or the 31 bp EcoRV-FokI fragment (lane 3) were added to the binding reaction. (d) gel retardation pattern using the EcoRV-FokI fragment from wild-type (lane 1) and mutant (lanes 2, 3 and 4) 35S promoters. FP=free probe, LB-lower band, UB=upper band.

FIGS. 8a–8d. The OCS element of the Ti-plasmid ags gene. (a) the cloned synthetic ags 19mer, oliags, and the cloned ocs 16mer, oliEB. The restriction sites indicated by single or double letters correspond to the polylinker sites of pUC18. (b) gel retardation. 64 bp HaeIII-Alu1 probe from the ags promoter (lanes 1–4), EcoRI-HindIII probe of oliags (lanes 5 and 6). Competitors were ocs promoter fragment (lane 2), ocs 16mer (lanes 3 and 6) and pUC polylinker (lanes 4 and 5). (c) Competition of binding to ocs 26mer probe—no competition (lane 1), pUC polylinker (lane 2) and 64 bp HaeIII-Alu1 fragment of ags promoter. (d) transient expression analyses of deletions of the ags promoter and adh1 promoter reactivation using oliEB (ocs 16mer) and oliags (ags 19mer). The cat enzyme activity relative to the −295.ags construct or the ocs-adh1 construct are indicated and are the average of three experiments. Cm=chloramphenicol and acCM=acetylated chloramphenicol. The structure of the chimeric genes and deletion end-points are indicated schematically. Maize adh1 promoter sequences are shown stippled. Numbering for the ags promoter are relative to its start of translation.

FIGS. 9a–9d. The OCS element in the nos promoter. (a) Promoter fragments used for gel retardation and expression studies. The restriction sites indicated by single or double letters, correspond to the polylinker sites of pUC18. (b) Gel retardation of probes made from the fragments shown in (a). (c) competition study using an ocs 16mer probe with no competitor (lane 1), pUC polylinker (lane 2) and pNOS-SH50 (lane 3). (d) Transient expression analysis showing activation of a maize adh1 promoter by the pNOS-SH50 fragment, the pNOS-XP21 fragment and a 48 bp ocs promoter fragment containing the 16 bp palindrome. Black boxes are the OCS elements, striped boxes are flanking nos promoter sequences and stippled boxes are the flanking ocs promoter sequences. Numbers above the constructs are the coordinates of the adh1 promoter and the numbers below the line are the coordinates of the ocs or nos promoter fragments. Numbering is relative to the start of transcription of the ocs, nos and maize adh1 genes. Cat activity, expressed relative to the OCS enhancer construct, are the averages of four experiments.

Figure 3:
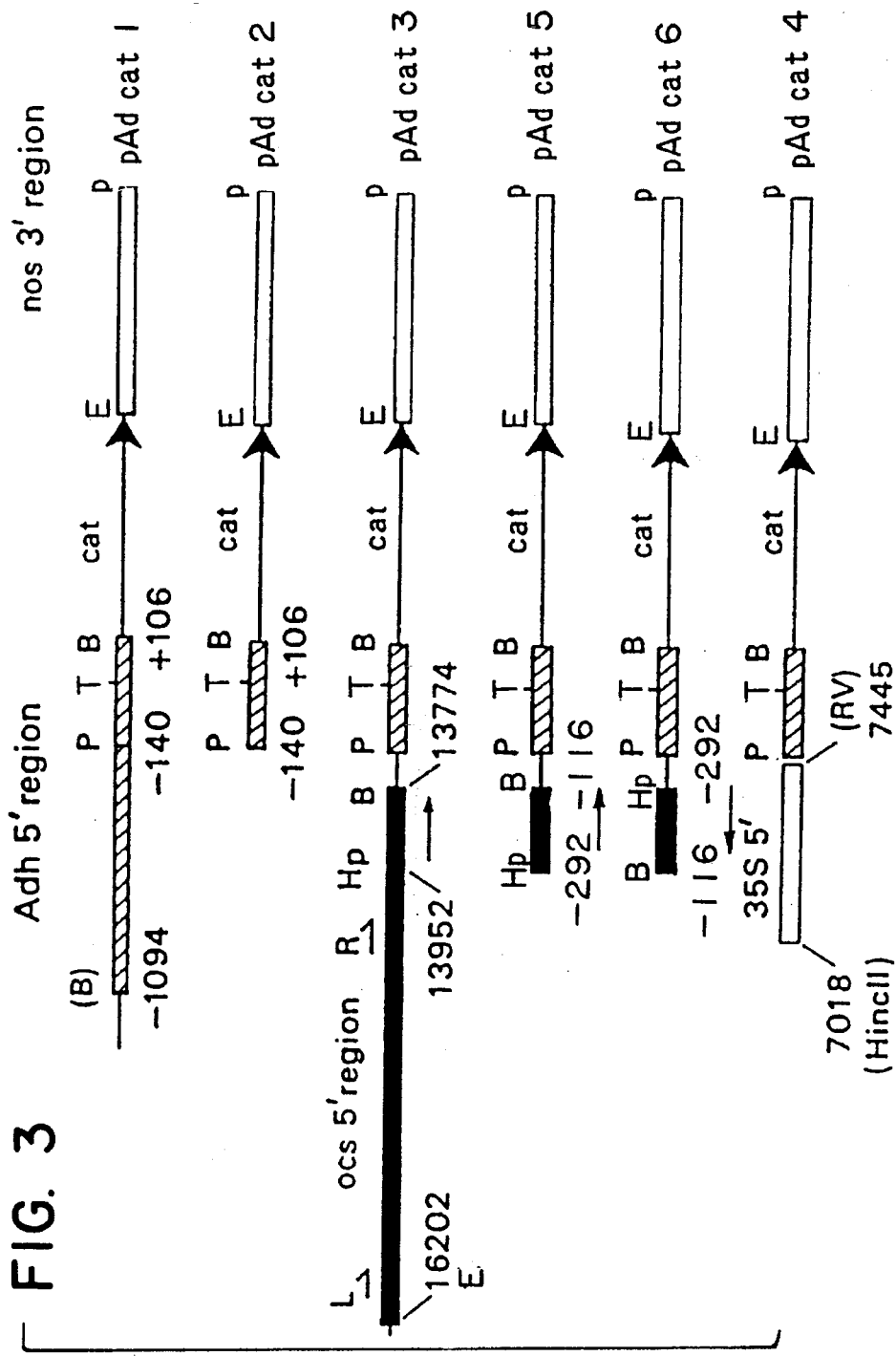
FIG. 3 shows the series of pAdCAT plasmids 1–6 and the included components of the transcriptional activating element/promoter/structural gene/polyadenylation signal complex. The construction of these plasmids was achieved by recombinant DNA technology as described in the examples. Restriction sites are designated by letters: B, BamHI; E, EcoRI; Hp, HpaII, RV, EcoRV; P, PstI. Letters in brackets are sites filled in with the Klenow fragment of PolI; ocs= octopine synthase; nos=nopaline synthase; cat=chloramphenicol acetyl transferase. Nucleotide coordinates for ocs DNA are from R. Barker et al. (1983) *Plant Mol. Biol.* 2:335–350; and those for CaMV 35S DNA are from A. Franck et al. (1980) *Cell* 21:285–294.

A. Binding reactions with different probes: Maize extract was mixed with [poly(dI-dC)-poly(dI-dC)] and incubated with various probes; lane 1, a 67/bp EcoRI-HindIII fragment containing the OCS element with flanking sequences from the pUC118 polylinker site; lane 2, a 58-bp XhoI-HpaI fragment containing the OCS element and ocs gene flanking sequence; lane 3, a 52-bp XhoI-SalI fragment from the promoter of the ocs gene lacking the element; and lane 4, a 54-bp PstI-SalI fragment from the maize alcohol dehydrogenase 1 gene containing the anaerobic regulatory element. The fractionated DNA is indicated as ub, upper band; lb, lower band; fp, free probe.

B. Binding reactions using specific and nonspecific unlabeled DNA fragments as competitors of the binding activity. The probe, the 67-bp EcoRI-HindIII fragment containing the OCS element, was incubated with extract and [poly(dI-dC)-poly(dI-dC)] after being mixed with: no competitor (land 1); specific competitor, the unlabelled probe at 5- (land 2), 50-

(lane 3), 500- (lane 4) fold molar excess; nonspecific competitor, the 80 bp HaeIII-HaeIII pUC18 fragment at 5- (lane 5), 50- (lane 6), 500- (lane 7) fold molar excess.

Figure 11C:
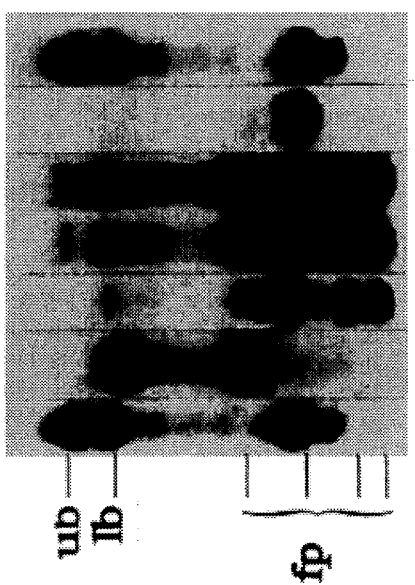
Figure 11B:
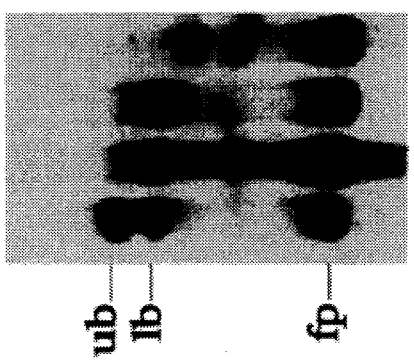
Figure 11A:
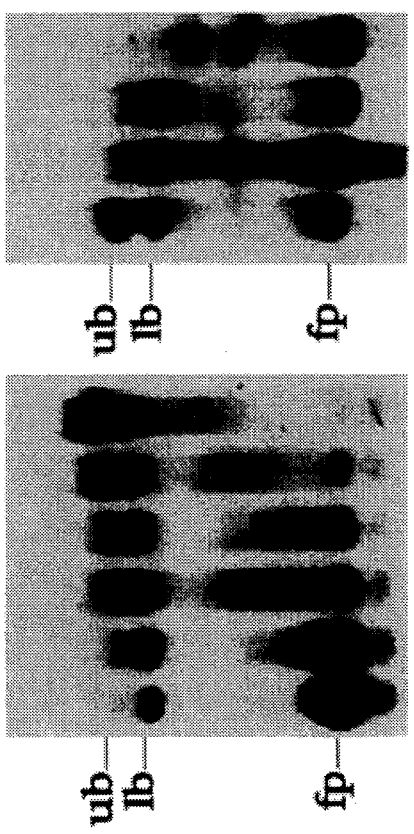

FIGS. 11a–11c. Gel retardation analysis of the relationship of the upper and lower bands.

A. Titration of extract and carrier DNA in the binding reaction. Binding reactions contained maize nuclear extracts at 4 μg (lanes 1–3) and 8 μg (lanes 4–6) of protein, [poly(dI-dC)-poly (dI-dC)] as carrier DNA at 1.0 μg (lanes 1, 4), 0.5 μg (lanes 2, 5) and 0.3 μg (lanes 3, 6) and the OCS element probe used in FIG. 1A, lane 1.

B. The mutated OCS elements as probes. Binding reactions contained maize nuclear extracts with 8 μg of protein, [poly(dI-dC)-poly(dI-dC)] at 1.0 μg and the 123-bp PvuII-SalI fragments with various OCS elements as probes: lane 1, wild-type; lane 2, mutant 3.3; lane 3, mutant 6.1; and lane 4, mutant 5.1.

C. Reconstruction of upper band complex from lower band activity. The lower band complex was generated by a binding reaction using the 123-bp probe containing the mutant 6.1 OCS element followed by fractionation of the reaction mixture. The lower band complex was electroeluted from an excised gel piece, and a portion refractionated (lane 2). The remaining eluate was treated with 1M NaCl, HindIII and wild-type OCS element probe diluted to 0.1M NaCl, incubated at 30° for 30 minutes and dialyzed into Binding Buffer. The mixture was refractionated at 0.1, 0.2 and 0.3 final volume to show respectively the various cut and uncut free probes (fp) (lane 3), and the lower and upper band complexes (lanes 4 and 5). A gel piece corresponding to the lower band complex was generated by the fractionation of a binding reaction done in the absence of probe. The electroeluted components were refractionated after treatment with HindIII and wild-type OCS element probe (lane 6). Lanes 1 and 7 mark the upper (ub) and lower bands (lb) from the fractionation of a standard binding reaction with the wild-type OCS element.

Figure 12A:
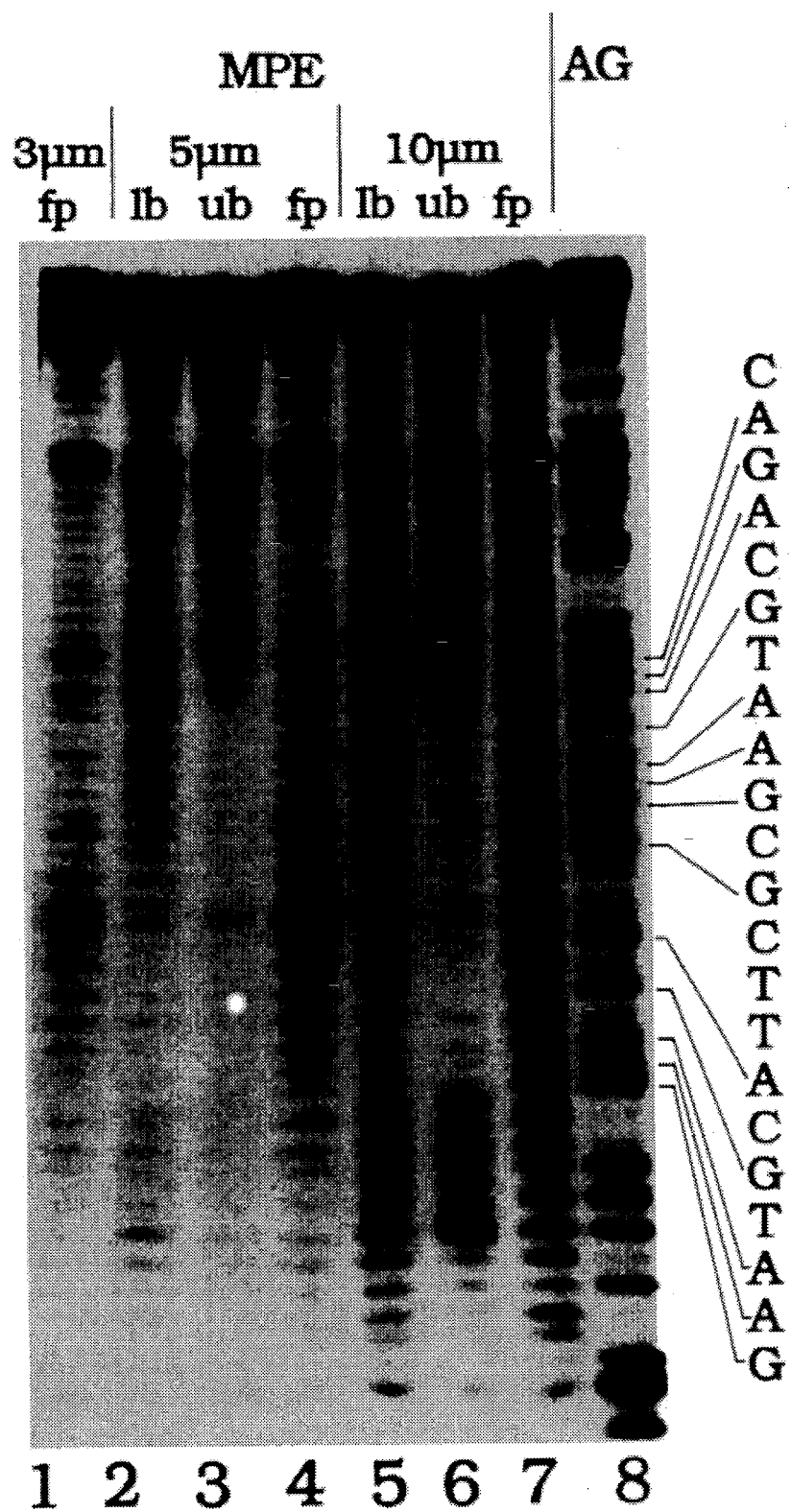
Figure 12B:
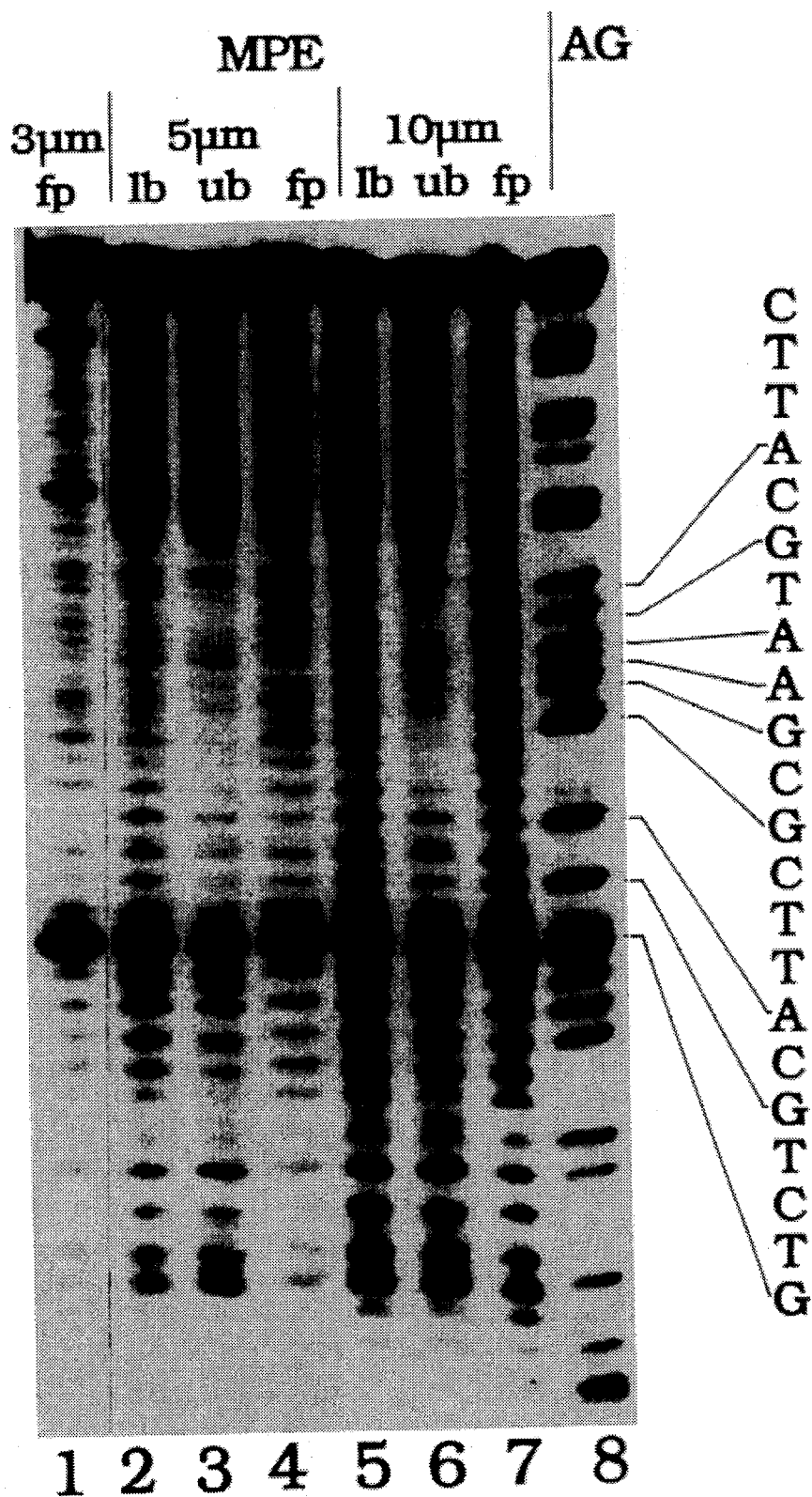
Figure 12C:
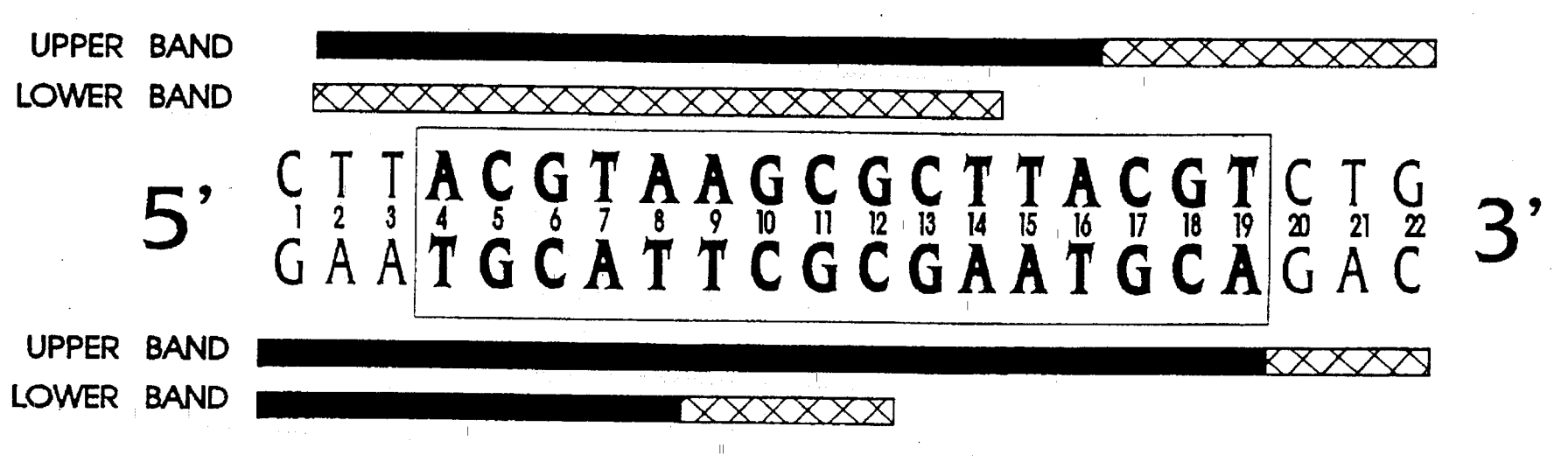

FIGS. 12a–12c. MPE footprint of the wild-type OCS element, free probe, lower and upper band. A. Bottom strand. B. Top strand. Protein-DNA complexes generated by the binding reaction were treated with 3 μM (free probe only, lane 1, 5 μM (lanes 2–4), and 10 μM MPE (lanes 5–7). Lanes 2 and 5, lower band; lane 3 and 6, upper band; lanes 1, 4 and 7, free probe and lane 8, sequence marker, A+G reaction. C. Summary of the footprint protection. Complete protection is indicated by a solid horizontal bar and partial protection by a hatched bar. The sequence is that of the 16-bp OCS element (within box) in the pUC118 polylinker.

Figure 13A:
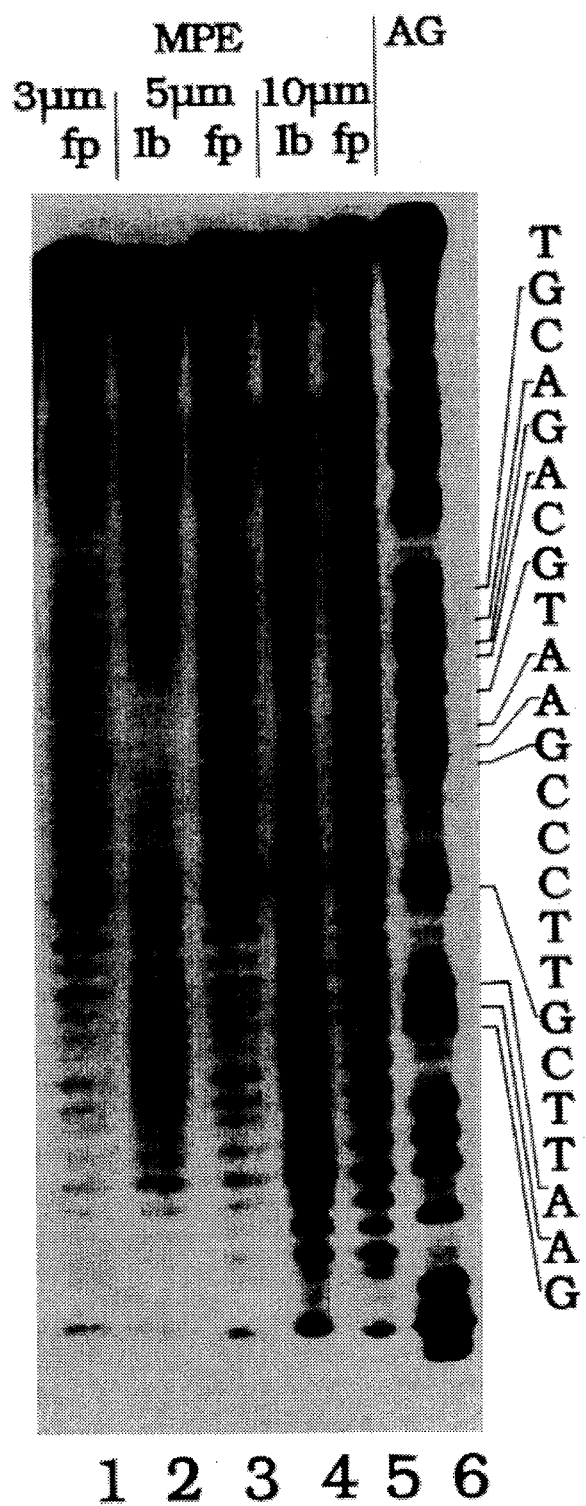
Figure 13B:
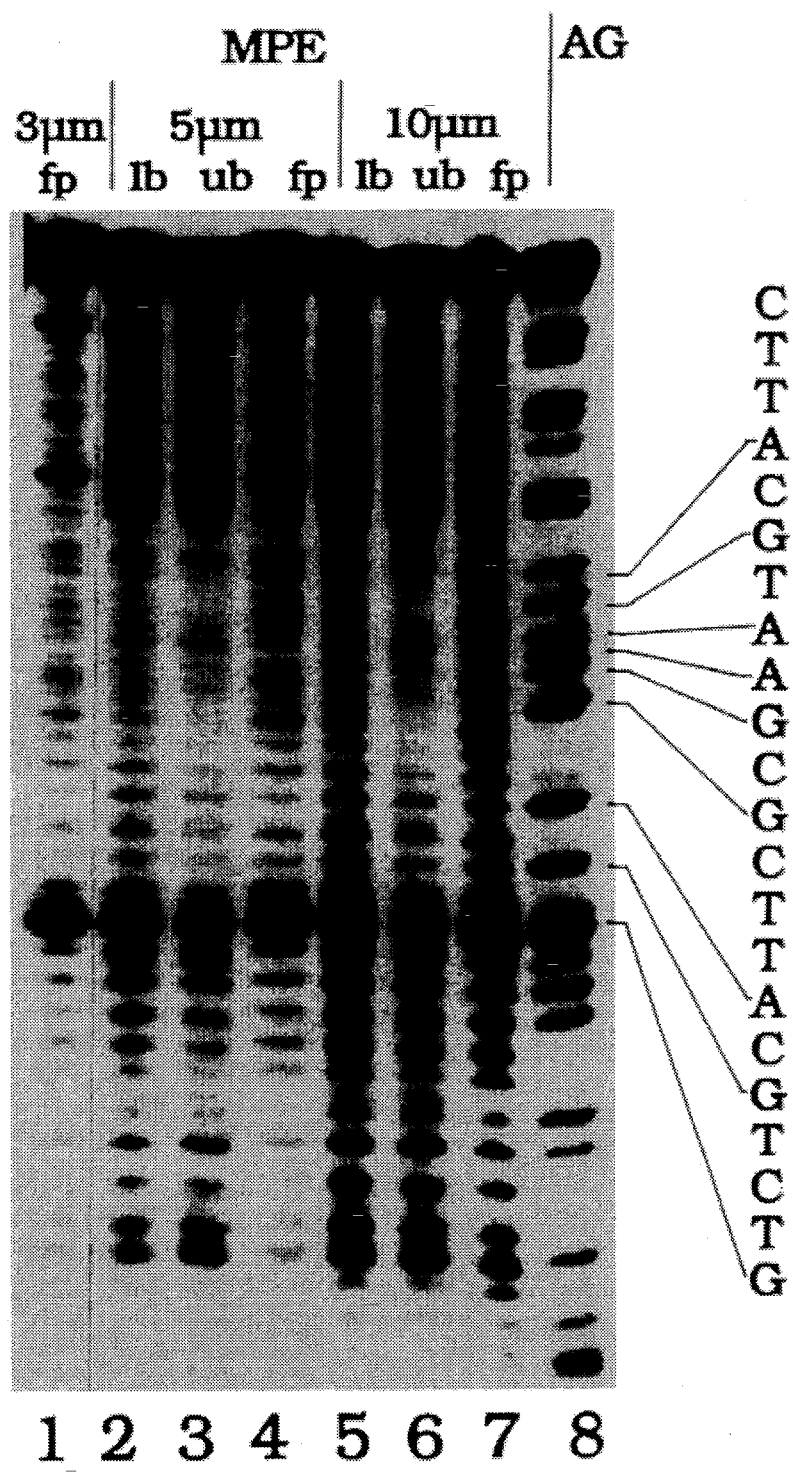

FIGS. 13a–13c. MPE footprint of the 3.3 mutant OCS element, free probe and lower band. A. Bottom strand. B. Top strand. Protein-DNA complexes generated by the binding reaction were treated with 3 μM (free probe only, lane 1), 5 μM (lanes 2 and 3) and 10 μM (lanes 4 and 5) MPE. Lanes 2 and 4, lower band; lanes 1, 3, 5, free probe; lane 6, sequence marker, A+G reaction. C. Summary of the footprint protection. Symbols are as in FIG. 3.

Figure 14:
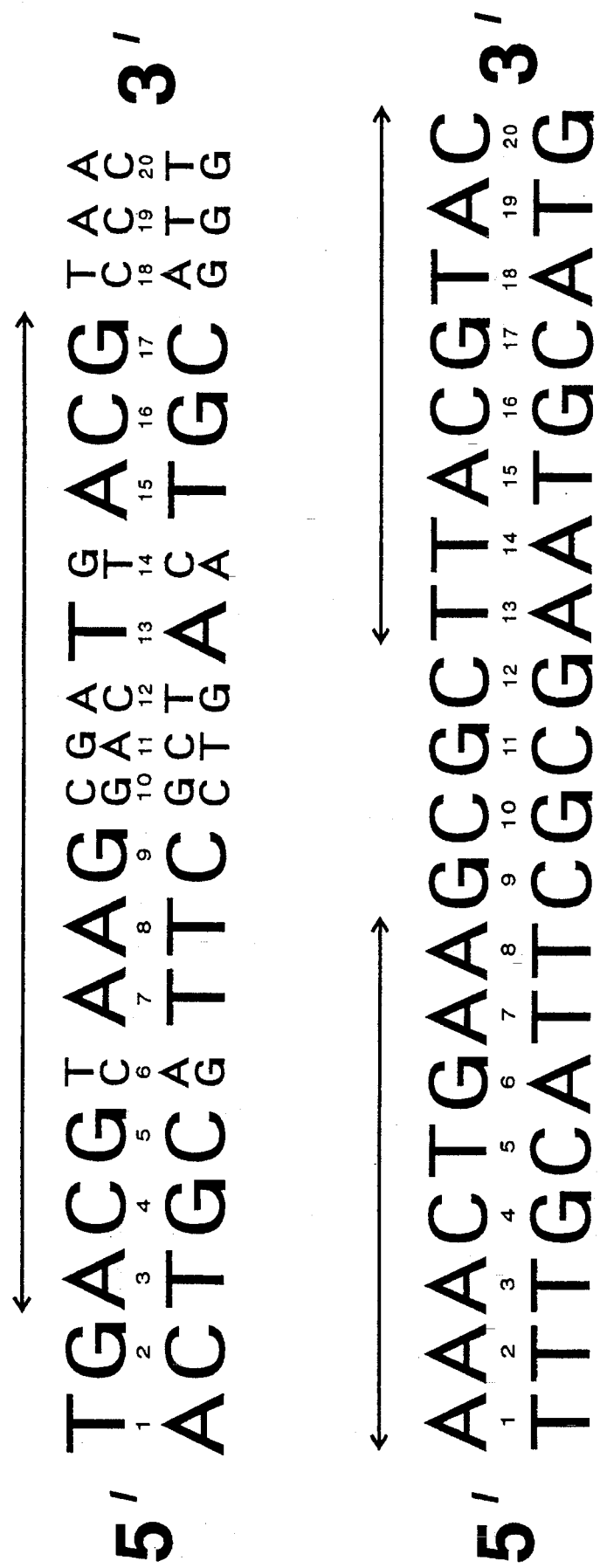

FIGS. 14a–14b. A. The 20-bp consensus sequence. The arrow indicates the 16-bp OCS element. B. The 20-bp OCS element as it occurs in the ocs gene. The sequence is from De Greve et al. (1983) J. Mol. Appl. Genet. 1:499–511. The arrows indicate an imperfect palindrome motif.

DETAILED DESCRIPTION OF THE INVENTION

The following definitions are provided in order to remove ambiguities as to the intent or scope of their usage in the specification and claims.

Expression refers to the transcription and translation of a structural gene so that a protein is made.

The terms enhancer, enhancer element, or transcription activating element (TAE) refer to DNA sequences capable of activating or enhancing gene expression. The term plant enhancer element or OCS element as claimed herein refers to a DNA sequence capable of activating or enhancing expression of a structural gene in a plant cell, plant tissue or a plant, and also having a binding site for the ocs factor. The plant enhancer element hereof can be the DNA sequence originally discovered within the ocs 5' untranscribed region and associated with the ability to increase the expression level of a downstream gene. The OCS element consensus nucleotide sequence associated with that functional plant enhancer element is identified by the nucleotide sequence

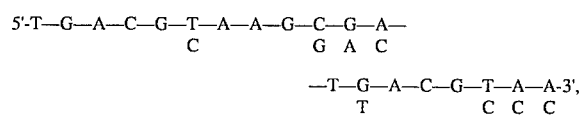

and includes the reverse sequence thereof and sequences with about 60% or greater, and preferably about 75% or greater homology to said sequence or its reverse. It is these sequences of DNA which can, in an orientation-independent fashion, enhance (increase) or activate transcription of nearby genes in plants. The TAE is preferably located from just above the promoter TATA box to about 1500 bp, and ideally from about 50 and about 500 bp, 5' to the transcription start site. The TAE may include as an optional second component, preferably placed within about 500 bp, and more preferably within about 20 to 100 bp of said primary component, the DNA sequence 5'-GATGTTAACATC-3', or its reverse sequence. Sequences with about 50% or greater, and preferably about 75% or greater homology to said sequence or its reverse which function to increase expression of associated genes in combination with said consensus sequence are considered equivalent thereto. The TAE may be used as a chemically synthesized oligonucleotide comprising the aforementioned sequences, or a segment of naturally occurring DNA containing the sequences.

Activating gene expression means that associated gene expression is observed when the plant enhancer element is present and not observed when it is not present. Enhancing gene expression means that gene expression is observed to be greater when the plant enhancer element is present than when it is not, and includes the case where gene expression is activated.

The reverse sequence of a given sequence is a sequence generated by writing the given sequence backwards (e.g., the reverse sequence of 5'-CAT-3' is 5'-TAC-3'.

The term consensus nucleotide sequence refers to a sequence having variable and invariable bases. The consensus sequence claimed herein as a plant enhancer element is the enhancer sequence similarity extending over twenty base pairs found in the 5' untranscribed promoter region of seven opine synthase genes and three plant viral genes (FIG. 4).

The term ocs or octopine factor refers to a protein or proteins present in maize nuclear protein extracts that binds to the 16 bp palindrome of the ocs promoter disclosed herein as a plant enhancer element. This ocs factor binds to the plant enhancer elements exemplified herein and also to any functional plant enhancer element within the scope of this invention. This factor is also called ocs transcriptional factor.

ocs transcriptional factor binding site refers to a specific nucleotide sequence associated with an OCS element to which an ocs Transcriptional factor will bind.

Promoter refers to sequences at the 5'-end of a structural gene which direct the initiation of transcription. Promoter sequences are necessary, but not always sufficient, to drive expression of the downstream structural genes. The promoter itself may be a composite of segments derived from more than one source, naturally occurring or synthetic. Eukaryotic promoters are commonly recognized by the presence of DNA sequences homologous to the canonical form 5'-TATAA-3' (TATA box) about 10–30 bp 5' to the location of the 5'-end of the mRNA (cap site, +1). About 30 bp 5' to the TATA box another promoter component sequence is often found which is recognized by the presence of DNA sequences homologous to the canonical form 5'-CCAAT-3' (R. Breathnach and P. Chambon (1981) *Ann. Rev. Biochem.* 50:349–383). In plants there may be instead a sequence known as the AGGA box, named for a symmetrical placement of adenosine residues around the triplet GNG (J. Messing et al. (1983), in *Genetic Engineering of Plants*, T. Kosuge et al. (eds.), Plenum Press, pp. 211–227).

The term heterologous, referring to a plant enhancer element, promoter, gene or structural gene being heterologous to another such element, means that the elements are derived from different sources. The term "not in its natural association" referring to such elements, means that the elements referred to may or may not be from the same source but are not in the same position with respect to such elements as in nature.

Polyadenylation signal refers to any nucleic acid sequence capable of effecting mRNA processing, usually characterized by the addition of polyadenylic acid tracts to the 3'-ends of the mRNA precursors. The polyadenylation signal DNA segment may itself be a composite of segments derived from several sources, naturally occurring or synthetic, and may be from a genomic DNA or an mRNA-derived cDNA. Polyadenylation signals are commonly recognized by the presence of homology to the canonical form 5'-AATAA-3', although variation of distance, partial "readthrough", and multiple tandem canonical sequences are not uncommon (J. Messing et al. supra). It should be recognized that a canonical "polyadenylation signal" may in fact cause transcriptional termination and not polyadenylation per se (C. Montell et al. (1983) *Nature* 305:600–605).

Structural gene refers to that portion of a gene comprising a DNA segment coding for a protein, polypeptide or portion thereof, possibly including a ribosome binding site and/or a translational start codon, but lacking at least one component of 5' sequence which drives the initiation of transcription. The structural gene may be one which is not normally found in the plant cell at all or in the location at which it is introduced, in which case it is termed a heterologous structural gene. A heterologous structural gene may be derived in whole or part from any source known to the art, including a bacterial genome or episome, eukaryotic nuclear or plastid DNA, cDNA, viral DNA, or chemically synthesized DNA. It is further contemplated that a structural gene may contain one or more modifications in either the coding segments or in the untranslated regions which could affect the biological activity or the chemical structure of the expression product, the rate of expression or the manner of expression control. Such modifications include, but are not limited to, mutations, insertions, deletions, and substitutions of one or more nucleotides. The structural gene may constitute an uninterrupted coding sequence or it may include one or more introns, bounded by the appropriate plant functional splice junctions. The structural gene may be a composite of segments derived from a plurality of sources, naturally occurring or synthetic. The structural gene may also produce a fusion protein. It is contemplated that the introduction into plant tissue of recombinant DNA molecules containing the enhancer/promoter/structural gene/polyadenylation signal complex will include constructions wherein the structural gene and its promoter are not derived from the same kind of plant as well as additional copies of naturally-occurring genes under enhancer control.

Plant tissue includes differentiated and undifferentiated tissues of plants including, but not limited to, roots, shoots, leaves, pollen, seeds, tumor tissue, such as crown galls, and various forms of aggregations of plant cells in culture, such as embryos and calli. The plant tissue may be in planta or in organ, tissue, or cell culture.

Derived from is used herein with the meaning of "taken from" or "obtained from."

Chemically synthesized, as related to a sequence of DNA, means that the component nucleotides were assembled in vitro. Manual chemical synthesis of DNA may be accomplished using well established procedures (i.e., Caruthers (1983) in *Methodology of DNA and RNA Sequencing*, Weissman (ed.), Praeger Publishers (New York) Chapter 1), or automated chemical synthesis can be performed using one of a number of commercially available machines.

Regulatory control refers to the modulation of gene expression by sequence elements upstream of the transcription start site. Regulation may result in an on/off switch for transcription, or it may result in variations in the levels of gene expression. To place a gene under regulatory control of sequence elements means to place it sufficiently close to such sequence elements that the gene is switched on or off, or its level of expression is measurably varied. In this invention, the enhancer sequences are preferably placed within about 1500 bp of the structural gene and upstream therefrom.

A transformable plant cell is any plant cell capable of having DNA inserted therein by any technique known to the art, and capable of expressing said DNA under any conditions known to the art to produce expression.

Homologs of structural genes, enhancer or regulatory sequences, or other sequences are homologous sequences that are functionally equivalent thereto, and have at least 50%, and preferably 75% homology thereto. Such sequences may be identified by those skilled in the art by the ability of their nucleic acids to cross-hybridize under conditions of appropriate stringency as is well understood in the art (as described in Hames and Higgins (eds.) (1985) *Nucleic Acid Hybridisation*, IRL Press, Oxford, UK). It will be understood that there may be minor sequence variations within sequences or fragments used or disclosed in this application. These variations may be determined by standard techniques to enable those of ordinary skill in the art to manipulate and bring into utility the functional units of the regulatory elements, the promoter elements necessary to direct the initiation of transcription, and the structural gene followed by a plant-expressible transcription termination (and perhaps polyadenylation) signal. Homologs as defined above are equivalent to the elements to which they are homologous and are included within the scope of the claims hereof naming said elements.

The identification and characterization of the transcription activating element in the promoter of the ocs gene involved the following general steps:

1. Cloning a 176 bp fragment of DNA from the upstream flanking region (−294 to −116) of the ocs gene in a construction where it was inserted upstream of the maize alcohol dehydrogenase 1 (adh1) promoter. Expression from that promoter in a transgenic tobacco host was dependent on the presence of this ocs-derived fragment, thus demonstrating that this fragment carried transcription activating capability.

2. Demonstration that the transcription activating capability of the ocs-derived fragment of DNA was not dependent on its orientation relative to the downstream promoter sequences.

3. Analysis of the nucleotide sequence of the ocs-derived fragment to reveal two palindromic sequences: 5'-ACGTAAGCGCTTACGT-3' and 5'-GAGTTAACATC-3'.

4. Deletion analysis of the ocs-derived fragment to determine that the presence of the 16 bp palindromic sequence was required for the activation of transcription of the downstream promoter. This established the sequence 5'-ACGTAAGCGCTTACGT-3' as the primary component of the transcription activating element. The 12 bp palindrome (second component) could be removed without greatly reducing transcriptional activation.

5. Demonstration that the 16 bp palindromic sequence (primary component), inserted as a synthetic oligonucleotide, was sufficient to activate the transcription from a downstream promoter, and thus enhance expression of a structural gene.

6. Demonstration that the 16 bp transcription activating element could increase the expression of other promoters.

7. Demonstration that the 16 bp transcription activating element had activity in monocotyledonous as well as in dicotyledonous plant hosts.

8. Discovery of sequences homologous to the 16 bp palindromic element of the ocs. promoter in the promoter regions of ten promoters from T-DNA opine synthase genes or plant viral genes (FIG. 4). These sequences were found from 27 to 146 bp upstream of their respective TATA boxes (FIG. 4). The octopine synthase promoter studied by Ellis et al. (1987) *EMBO J.* 6:3203–3208, concentrated on a specific, precisely defined cis-regulatory sequence, the 16 bp palindromic OCS element. The insertion of synthetic oligonucleotides containing the OCS element upstream of the maize adhI promoter, inactivated by deletion, reactivated the expression of this promoter in maize and tobacco protoplasts. This assay system has also been used to study the effect of mutations introduced into the OCS element on transcriptional enhancement and interactions with nuclear protein extracts (Ellis et al. (1987) *EMBO J.* 6:3203–3208; Singh et al. (1989) *Proc. Natl. Acad. Sci.* 86:3733–3737).

Schleif et al. (1988) *Science* 241:1182–1187 also showed in other systems that gene expression is modulated at the transcriptional level by the interaction of trans-acting proteins with specific cis-regulatory DNA sequences. Some of these cis-regulatory sequences which are transcriptional enhancers have been shown to be organized from combinations of DNA sequence motifs, each of which bind proteins to generate transcriptionally active complexes (Ondek et al. (1988) *Nature* 333:40–45; Fromental et al. (1988) *Cell* 54:943–953).

The OCS element is a binding site for a nuclear protein factor present in maize and tobacco nuclei (Singh et al. (1989) supra). Gel retardation assays using labelled DNA fragments from the ocs promoter or from cloned synthetic oligonucleotides containing the 16 bp palindrome revealed two specific retarded bands of different mobility resulting from the interaction between the DNA probe and a nuclear factor (Singh et al. (1989) supra). The same protein was involved in the two complexes, with a monomeric protein bound to the DNA probe in the faster migrating complex ("lower band") and a dimeric protein in the slower migrating ("upper band") complex. For convenience, this protein or proteins were referred to as the ocs factor. A set of mutant OCS elements containing one or more base changes introduced into the 16 bp palindrome by oligonucleotide synthesis, was analyzed by gel retardation assays and for enhancer activity in transient expression assays (Singh et al. (1989) supra). A strong correlation was observed between the presence of the upper band DNA-protein complex in gels and activation of transcription in vivo. In other words, association of two protein units with the OCS element is necessary for maximal transcriptional activation.

There are conflicting data in the literature regarding the extent of 5' sequence required for maximal expression of the nos gene. C. Koncz et al. (1983) supra, presented data that all signals required for maximal expression of the nos gene were in the 261 bp preceding the transcriptional start site. In contrast, C. Shaw et al. (1984) *Nucleic Acids Res.* 12:7831–7846, indicated that sequences further upstream than −88 were not essential for expression of nos in the Kalanchoe leaf and stem test system. G. An et al. (1986) *Mol. Gen. Genet.* 203:245–250, have more recently established that regions of nos upstream DNA including the TATA box (−26 to −19) and the CAAT box (−78 to −70) are required for efficient transcription, and that a sequence between −130 and −101 is absolutely required for expression in tobacco. Direct and indirect repeats are revealed in that publication; deletion analysis suggests that the pair of direct repeats (−171 to −161 and −137 to 127) and the pair of inverted repeats (−148 to −141 and −114 to −106) may regulate the level of downstream gene expression. More recently, Mitro and An (1989) *Mol. Gen. Genet.* 215:294–299 have reported that the 8 bp sequence (CAGAAACC) at −106 to 113 and its inverted repeat (GGTTTCTG) at −140 to 147 as well as a 10 bp potential Z-DNA-forming (Z) element are important for promoter function. Deletion of the Z element nullified promoter activity. Therefore, it appears that the Z element is an essential upstream regulator and the repeated elements are upstream modulators of the nos promoter.

Comparison of the OCS element regions of the ten promoters showed that the sequence similarity extends over twenty base pairs and that the 16 bp palindromic element originally described in the ocs promoter forms the core of this 20 bp element. In order to test whether these elements are functional OCS elements, these sites were also tested for their ability to bind to the OCS nuclear factor extracted from tobacco nuclei described by Singh et al. (1989) supra and to act as transcriptional activators in vivo. A sequence identical to 12 out of 16 bases of the 16 bp OCS element occurs at position −79 to −64 in the 35S promoter of the CaMV. The OCS element of the 35S promoter was found to be wound inducible. A deletion from −89 to −73 that removed approximately half of this sequence was shown to decrease the activity of the promoter 50 fold (Ow et al. (1987) *Proc. Natl. Acad. Sci.* 84:4870–4874). The sequence homologous to the OCS element also overlaps the pentanucleotide direct repeat TGACG observed by Fang et al. (1989) *The Plant Cell* 1:141–150. Sequences homologous to the OCS element also occur in the genome of two other caulimoviruses, FMA and CERV. These two viruses have a similar genomic organization to CaMV and the potential OCS elements occur in the intergenic promoter region that is highly conserved between the three viruses (Richins et al. (1987) *Nucl. Acids Res.* 15:8451–8466). The TGACG direct repeat occurs in the FMV genome and with a single mismatch in the CERV genome. In each case the pentanucleotide repeats are separated by 7 bp.

Sequences homologous to the OCS element occur in six other T-DNA genes. A 12 out of 16 match is found in the promoter of the nopaline synthase gene. A 13 out of 16 match occurs in the T-DNA of the Ri-plasmids of Agrobacterium rhizogenes strain A4 approximately equidistant from the transcription starts in the two divergent genes, MAS1' and MAS2' which are involved in the biosynthesis of mannopine. Two homologous sequences occur close to the TATA boxes in the promoters of the equivalent mannopine synthase genes MAS1' (9/16 match) and MAS2' (10/16 match) that occur in the T-DNA of octopine Ti-plasmids (Velten et al. (1984) *EMBO J.* 3:2723–2730). In the MAS2' promoter, direct repeats of TGACG are present with 7 bp spacing. Both published sequences (Velten et al. (1984) supra; Barker et al. (1983) *Plant Mol. Biol.* 2:335–350) differed in this region. Resequencing this region of pTiAch5 confirmed the sequences shown in FIG. 4. Another sequence was detected in the promoter of the agropine synthase gene in the T-DNA of an octopine Ti plasmid (Barker et al. (1983) supra). The homology with the ocs palindrome is only 8 out of 16 but the direct repeat of the pentanucleotide TGACG occurs with a spacing of 7 bp between the repeated units.

No obvious homology was detected in other T-DNA promoters, including the agropine synthase promoter of the Ri-plasmid, pRiA4.

The protein binding capacity of the OCS elements were tested. Gel retardation and footprint analyses were used to characterize the specific interaction with proteins present in maize or tobacco nuclear extracts. Mutated OCS elements which exhibited little transcriptional enhancing activity in vivo, but formed protein-DNA complexes in vitro (Singh et al. (1989), supra), were used to identify the protein binding sites within the OCS element. The OCS element was shown to have more than one binding site associated with the consensus nucleotide sequence for the same ocs transcription factor.

The conclusion that the OCS element is comprised of a 20 bp sequence is supported by results from footprinting experiments on the ocs promoter which reveal a protected region larger than 16 bases and by the fact that the minimal element from the nos promoter that gave double-band binding was 20 bp long. A considerable degree of sequence divergence occurs between the 10 OCS element sequences in FIG. 4. The natural sequence flexibility at this protein binding site is consistent with the saturation mutagenesis study of Singh et al. (1989) supra where it was demonstrated that the majority of single and double base substitutions within the 16 bp palindrome of the ocs promoter had little effect on enhancing activity of the sequence. Although divergence occurs between the different 20 bp sequences, a high degree of conservation is observed at positions 3, 4, 5 and 13, 15, 16, 17. Mutation of ACG to TAT at position 3–5 had a drastic effect on activity of the 35S promoter, indicating that this motif is of critical importance in this context. In the nos promoter, however, this region is AGC. Here the divergence from the conserved ACG motif is possibly compensated for by the TG dinucleotide at positions 1 and 2 of the OCS element. This explanation is supported by the effect of mutations or deletions of the 5' TG dinucleotide at positions 1–2 of the nos sequence that profoundly affect the stability of the DNA-protein complex and almost completely eliminate the upper band complex in gel retardation assays. The existence of sequence variation between the 10 OCS elements raises the question of their relative affinity for the ocs factor and strength as promoter elements. Apart from sequence variation, there is also considerable variation in their distance from their respective TATA boxes, ranging from 26 to 146 base pairs. This may also quantitatively affect the contribution of the different elements to overall promoter activity.

A 20 bp consensus sequence for the OCS element was derived from the alignment of the 10 sequences (FIG. 4). The consensus can be viewed in several ways: as a 20 bp palindrome with two 10 bp half sites or as two 8 bp direct repeats separated by 4 bases. The 20 bp palindrome is an extension of the 16 bp palindrome in the promoter of the ocs gene. The 8 bp direct repeats overlap the pentanucleotide direct repeats of the 35S promoter noted by Fang et al. (1989) *The Plant Cell* 1:141–150. The distinction between recognition of direct repeats versus inverted repeats could be of critical importance in trying to understand the way the protein factor(s) bind to the OCS element and how they interact with each other to produce the double band binding pattern observed in gel retardation assays.

Both the spacing between the two halves of the recognition sites and the sequence of the central region appear to be critical for protein binding and enhancer activity of these elements: it was previously shown that a 4 bp insertion in the center of the OCS element destroyed its enhancer activity (Ellis et al. (1987) *EMBO J.* 6:3203–3208) incorporated herein by reference. A 2 bp insertion made by filling in the TagI site at the center of the OCS element of the ags promoter prevented the formation of the upper band complex in gel retardation. Single base deletions within the palindrome also inactivated the OCS element (Singh et al. (1989) supra). The loss of upper band binding was correlated with loss of activity in mutant 2 of the 35S promoter (FIG. 5). These results also agree with those of Singh et al. (1989) supra that showed that the upper band complex is essential for enhancer activity of the 16 bp palindrome. The role of the central bases of the OCS element are more important than just spacers. Sequence changes in the central region of the 16 bp palindrome of the ocs promoter showed that the identity of these central bases was also of importance to the function of the OCS element (Singh et al. (1989) supra).

Further, the gel retardation assays with nuclear extracts of maize showed the presence in maize nuclear extracts of a protein that binds specifically to the OCS element. The formation of two retarded bands raised the possibility that more than one protein species interacts with the palindrome or that there are two binding sites in the OCS element for the one protein. Mutant palindromes with sequence alterations restricted to one-half of the inverted repeat were unable to form the higher molecular weight band indicating that each half of the palindrome sequence contains a single binding site.

It was believed, therefore, that the wild-type palindrome contains two binding sites, and when both sites bind the protein a higher molecular weight complex would be evident in retardation assays. This interpretation was given direct support in a reconstruction experiment which demonstrated that the DNA-binding protein recovered from the lower molecular weight band was subsequently able to produce both lower and upper bands with newly added DNA sequence.

The DNA-binding protein has been identified as the ocs Transcription Factor (OCSTF) by Singh et al. (1989) who showed that transcriptional enhancement in vivo was correlated with the presence of upper bands in gel retardation assays. This correlation indicated that the two binding sites have to be occupied in order that the element/protein complex functions as an enhancer. Although it was shown in the instant specification that an intact half-element was recognized by OCSTF but was incapable of transcriptional activation, the prospect exists that, in a different sequence context, a half-element may function. For example, a motif corresponding to one-half of the estrogen responsive element (ERE) which is normally nonfunctional, does function as an ERE in the ovalbumin promoter at a specific position relatived to the TATA box (Tora et al. (1988) *EMBO J.* 7:3771–3778).

The two binding sites, one in each half of the palindrome, would be expected to have equal affinity for the protein. The footprint analyses did not support this expectation in that protein was shown to bind preferentially to the 5' half of the palindrome. The extension of DNA protection, at least two base pairs on each side of the element, indicates that the effective element is 20-bp rather than 16-bp. We conclude that the nucleotides flanking the designated 16-bp element differentially influence the binding affinities of the two binding sites.

This conclusion is compatible with the description in the instant specification of a number of elements related closely by sequence to the OCS element that competed with the OCS element for the same DNA-binding protein. The consensus sequence of this family of elements extended for 20-bp, the central 16-bp corresponding to the OCS element of FIG. 5A. In the mutation analysis of the OCS element, Singh et al. (1989) supra has found unequal transcriptional enhancing effects of identical mutations in comparable positions within the 5' and 3' halves of the palindrome. In light of the instant disclosure Applicants suggest that the asymmetry found in those experiments was a consequence of the different sequences flanking the 16-bp palindrome with the 5' half of the 20-bp sequence being closer to the consensus sequence than the 3' half. In a sequence element containing a 20-bp perfect palindrome, symmetric mutations would be expected to have identical consequences for protein binding, DNA protection patterns and transcriptional enhancement.

Figure 5B:
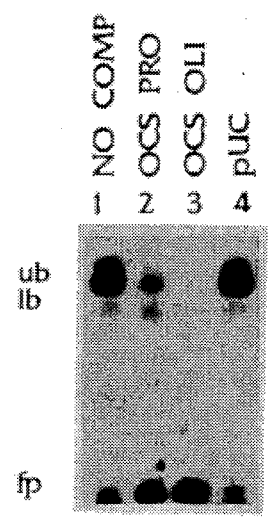

Examination of the 20-bp OCS element sequence shows that both direct and inverted repeats (or near repeats) can be identified (FIG. 5B). If the sequence motif that is recognized is a direct repeat then the unit binding protein for each site can be a monomer polypeptide. On the other hand, if each half of the 20-bp sequence has an 8-bp palindrome as indicated in FIG. 5B with a consensus sequence of TTACG-TAA and with 2 binding sites, then the binding unit can actually be a dimer of similar polypeptides. The functional transcriptional complex would then be composed of two dimer units binding to the 20-bp DNA sequence.

The interaction of dimeric proteins with cis-regulatory sequences with direct or inverted repeats has been suggested as a mechanism to increase selectivity of protein-DNA interactions (Schleif (1988) *Science* 241:1182–1187). However, the duplication of a single protein-DNA complex to double the size of the recognition site and therefore increase the affinity of the interaction requires a binding factor to be either a dimeric protein with two binding sites properly aligned, or a monomeric protein interacting cooperatively with a preexisting monomer-DNA complex. Duplication of the protein-DNA interaction in the OCS element may be a strategy to maintain selectivity of transcriptional activation. Activation of promoters containing the OCS element may require a precise positioning of two binding site motifs such that the juxtaposition of two binding factors allows the formation of a structure critical for a transcriptional complex.

The similarity of the OCSTF-DNA interactions seen with maize and tobacco nuclear extracts implies that OCSTF is conserved between monocots and dicots. The presence of OCSTF in plants such as maize, which is not infected by Agrobacterium, suggests that it predates both the Agrobacterium-dicot association and the monocot-dicot divergence. This wide distribution indicates that the OCSTF may be an essential component of the transcriptional regulation of one or more key enzymes or of some other fundamental cellular process.

Production of genetically modified plant tissue expressing a structural gene under control of an enhancer element and a downstream promoter combines the specific teachings of the present disclosure with a variety of techniques and expedients known in the art. In most instances, alternative expedients exist for each stage of the overall process. The choice of expedients depends on variables such as the choice of the vector system for the introduction and stable maintenance of the transcription activating element/promoter/structural gene/polyadenylation signal combination (the expression complex), the plant species to be modified and the desired regeneration strategy, and the particular structural gene to be used, all of which present alternative process steps which those of ordinary skill are able to select and use to achieve a desired result. For instance, although the starting point for obtaining the transcription activating element is exemplified in the present application by pTiAch5, homologous DNA sequences of other octopine-type Ti plasmids, or from different sources, might be substituted as long as the appropriate modifications are made to the procedures for manipulating the DNA carrying the enhancer element. Similarly, polyadenylation signals from the nos gene might be replaced by functional signals from other sources, again with appropriate procedural modifications. Homologs of structural genes or of other sequences may be identified by those of ordinary skill in the art by the ability of their nucleic acids to cross-hybridize under conditions of appropriate stringency as is well understood in the art. It will be understood that there may be minor sequence variations within sequences utilized or disclosed in the present application. These variations may be determined by standard techniques to enable those of ordinary skill in the art to use the functional units of transcription activating sequence, promoter elements, structural genes, and polyadenylation signals. The use of the anaerobically induced promoter from maize adh1 might be substituted by other DNA segments carrying promoter elements. As improved means are developed for the stable insertion of foreign genes in plant cells and for manipulating the modified cells, those of ordinary skill in the art will be able to select among those alternate process steps to achieve a desired result. Such means include, but are not limited to, electroporation, microinjection, and direct DNA transformation.

These techniques expand the range of plant cells into which DNA can be introduced. The remaining steps of the preferred embodiment for obtaining a genetically modified plant include inserting the enhancer/promoter/structural gene/polyadenylation signal combination into a T-DNA-containing vector, and transferring the recombinant DNA to a plant cell wherein the modified T-DNA becomes stably integrated as part of the plant genome. Techniques for in vitro culture and eventual regeneration into whole plants, which may include steps for selecting and detecting transformed plant cells, are included. Procedures for transferring the introduced gene from the originally transformed strain into commercially acceptable cultivars are known to those skilled in the art.

There are many examples of known sequences which modulate gene expression. In some cases, for example, the 6 bp core of the recognition sequence for the general amino acid control activator protein, GCN4, the conservation of sequence is critical to function. In other systems, the requirements are less stringent. Precedents for divergence of sequence with maintenance of function include the heat shock elements (HSE) sequences at the 5' ends of six Drosophila heat shock genes hsp268 and hsp27, wherein there are 7 of 14 and 9 of 14 matches to the HSE consensus sequence. For four other heat shock genes compared, homology to the consensus ranges from 11 to 13 out of 14 bases (H. Pelham and M. Bienz (1982) in *Heat Shock from Bacteria to Man*, M. Schlesinger et al. (eds.), Cold Spring Harbor Laboratory, pp. 43–48). Furthermore, although the idealized sequence of the HSE is palindromic, the numbers of bases within the actual HSE's in front of those six genes which could pair in a stem-loop structure varies. Another case where there is sequence divergence while functionality is maintained is in those E. coli DNA sequences which bind the cyclic-3', 5'-adenosine monophosphate (cAMP)-cAMP receptor protein complex. The DNA binding sites have been analyzed statistically to yield a 9 bp consensus sequence (5'-AA-TGTGA-T----C-3'), found over a span of 16 bp. In six pre-gene sites studied, 8 of 9 bases matched the consensus in each case (R. Ebright (1982) in *Molecular Structure and Biological Activity*, J. Griffin and W. Daux (eds.), New York: Elsevier Science Publishing Company, pp. 91–99). In the sequence analysis of eleven half-sites to which the bacteriophage lambda repressor binds, the matches to the consensus sequence ranged from 9 of 9 to as low as 5 of 9 (T. Maniatis et al. (1975) *Cell 5:109–113*). It is asserted herein that a DNA sequence with about 50% or greater, and preferably about 75% or greater homology to the 16 bp sequence identified as the primary functional component within the transcription activating element will function to increase or activate the level of expression of a nearby, preferably downstream, structural gene. As will be apparent to those skilled in the art, the effectiveness of different constructions having a given percent homology to said primary component may vary, as the positions of given bases within the 16 bp identifying sequence of the primary component of the transcription activating element varies. The relative effectiveness of variant constructions can readily be ascertained without undue experimentation using techniques of site-directed mutagenesis known to the art. Oligonucleotides with defined variant bases can be synthesized to substitute for the 16 bp palindromic sequence, so that positional importance of individual bases can be determined, and other known techniques can be employed for more random variations (reviewed in M. Smith (1985) *Ann. Rev. Genet.* 19:423–462). That about one-half of the palindromic 16 bp sequence is sufficient to activate downstream transcription is demonstrable by known molecular biological techniques, for example, by the synthesis and insertion of an appropriate 8 bp oligonucleotide.

A principal feature of the present invention in its preferred embodiment is the recombinant plasmid having an inserted heterologous promoter and heterologous structural gene whose transcriptional expression is enhanced by the OCS enhancer element, and in which transcription is terminated in response to the downstream polyadenylation signal. It has been determined that this transcription activating element is most effective 5' to the promoter, and that the active sequence should be placed between about 1500 bp upstream from the transcription initiation site and immediately 5' to the TATA sequence of the promoter, but that its orientation is not important to functionality. To be affected most strongly by the enhancer element-promoter complex, the structural gene must be inserted downstream of said complex. (A few known promoters exert bidirectional control, in which case either side of the promoter could be considered downstream.) That portion of the structural gene which ultimately codes for the amino terminus of the protein is the 5'-end of the gene, while that end which codes for amino acids near the carboxyl end is termed the 3'-end of the gene. The 5'-end of the structural gene is best located adjacent to the 3'-end of the enhancer element-promoter complex. The polyadenylation signal must be located in the correct orientation downstream from the 3'-end of the coding sequence. Another consideration is the distance between the functional elements of the expression complex. Substantial variation appears to exist with regard to these distances; therefore, the distance requirements are best described in terms of functionality. As a first approximation, reasonable operability can be obtained when the distances between functional elements are similar to those in the genes from which they were derived. An additional requirement in the case of constructions leading to fusion proteins is that the ligation of the two genes or fragments thereof must be such that the two coding sequences are in the same reading frame, a requirement well understood in the art. An exception to this requirement exists in the case where an intron separates the coding sequence derived from one gene from the coding sequence of the other. In that case, the coding sequences must be bounded by compatible splice sites, and the intron splice sites must be positioned so that the correct reading frame for both genes is established in the fusion after the introns are removed by post-transcriptional processing. Differences in rates of expression or developmental control may be observed when a given gene is inserted under the control of different transcription activating element-promoter complexes.

In the preferred embodiment the chloramphenicol acetyl transferase (cat) reporter gene has been inserted into the expression plasmid 3' to the transcription activating element-promoter complex at a BamHI site. As will be apparent to those of ordinary skill in the art, components of the expression complex may be joined by any naturally occurring or constructed restriction sites convenient for in vitro manipulations. Incompatible ends of restriction fragments may be converted to blunt ends for ligation, or modified by the addition of linkers or adaptors. The major consideration is that the sequences at the junctions maintain transcriptional and translational functionality.

EXAMPLES

The following examples are provided for illustrative purposes only and are not intended to limit the scope of the invention.

The examples utilize many techniques well known and accessible to those skilled in the arts of molecular biology, the manipulation of recombinant DNA in plant tissue, and the culture and regeneration of transformed plants. Enzymes are obtained from commercial sources and are used according to the vendors' recommendations or other variations known in the art. Reagents, buffers and culture conditions are also known to the art. References containing standard molecular biological procedures include Maniatis et al. (1982) *Molecular Cloning*, Cold Spring Harbor Laboratory, Cold Spring Harbor, New York; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, New York; Old and Primrose (1981) *Principles of Gene Manipulation*, University of California Press, Berkeley; Schleif and Wensink (1982) *Practical Methods in Molecular Biology*; Glover (ed.), (1985) *DNA Cloning* Vol. I and II, IRL Press, Oxford, UK; Hames and Higgins (eds.) (1985) *Nucleic Acid*

*Hybridization,* IRL Press, Oxford, UK; Setlow and Hollaender (1979) *Genetic Engineering: Principles and Methods,* Vols. 1–4, Plenum Press, New York, which are expressly incorporated by reference herein. Abbreviations and nomenclature, where employed, are deemed standard in the field and commonly used in professional journals such as those cited herein.

EXAMPLE 1

This example describes the cloning, transformation, and assay strategy for examining the expression of a reporter gene under the control of the maize adh1 anaerobically inducible promoter. Use of this system in both monocot and dicot hosts such as tobacco and maize enables one to detect inserted sequences with transcriptional activating activity.

1.1 Cloning of the maize adh1 promoter region

The maize adh1 anaerobically inducible promoter was prepared from a genomic clone, pIS.1 (E. Dennis et al. (1984), *Nucleic Acids Res.* 12:3983–4000) by BamHI and HindIII digestion. The adh1 promoter fragment contains 1200 bp 5' and 205 bp 3' of the ATG translation initiation codon. The fragment was ligated into pBR322 which had likewise been digested with BamHI and HindIII. The promoter fragment was shortened by cutting at a unique SacII site 11 bp 3' of the ATG codon, deleted using the 3'–5' exonuclease activity of T4 DNA polymerase, followed by S1 nuclease digestion to remove single- stranded ends, and repaired with the Klenow fragment of Polymerase I to ensure blunt ends. A synthetic HindIII linker was added, the plasmids were recircularized, and several randomly chosen representatives were subcloned into M13 for sequencing. Plasmid pAd1 was deleted to +106, 2 bp upstream of the A in the translation initiation codon, and the promoter fragment extended to −1094 in the 5' direction relative to the cap site.

1.2 Cloning of the polyadenylation signal

A plant polyadenylation signal was derived from the 3'-untranslated region of the nopaline synthase gene. The signal was obtained as a 1.7 kb EcoRI-PstI fragment of pLGV2382 (Herrera-Estrella et al. (1983) *EMBO J.* 2:987–995). This fragment was ligated to EcoRI and PstI-cut pAd1, the 5' BamHI site was filled in with Klenow fragment of Polymerase I, and the HindIII site was converted to a BamHI site using synthetic linkers to yield plasmid pad2.

1.3 Cloning of the chloramphenicol acetyl transferase gene pNOSCAT4 (L. Herrera-Estrella, personal communication) carries the chloramphenicol acetyl transferase gene of pBR325 (F. Bolivar (1978) Gene 4:121–136). (In the construction of pNOSCAT4, the TagI ends of the cat gene were converted to BamHI ends by the addition of linkers). pNOSCAT4 was cut with BamHI to release the cat-containing fragment which was ligated into pad2 cut with BamHI. The resultant plasmid was cut at its unique SalI site; this site was converted to a BglII site using the appropriate linker to generate pAdcat1, in which the adh1 promoter, the reporter gene, and the downstream polyadenylation signal are assembled in the correct orientations with respect to one another. pAdcat2 was constructed by inserting the PstI fragment containing the expression complex into PstI-cut pUC8.

An alternate source of the cat gene is Sau3A-cut pBR325; the cat gene resides on a fragment which carries 56 bp of 5' untranslated sequence, and can be ligated with BamHI-cut pad2. A third alternative is to isolated the appropriate TagI fragment of pBR325, and to add BamHI linkers.

1.4 Binary vector utilization for transformation of tobacco

The binary vector pGA472 (G. An et al. (1985) *EMBO J.* 277–284) is a T-DNA-containing vector which can replicate in both E. coli and A. tumefaciens, and can be mobilized between bacterial cells in triparental matings (G. Ditta et al. (1980) *Proc. Natl. Acad. Sci. USA* 77:7347–7351). From the Agrobacterium host it can be mobilized in trans by functions on the Ti plasmid into plants wherein it will promote stable integration into the genome via its T-DNA. pAdcat1 was inserted into pGA472 by cointegration at the unique BglII sites in each plasmid. pAdcat2 was similarly introduced by joining of the two plasmids at unique HindIII sites. These recombinant plasmids were selected in E. coli and were conjugated into *A. tumefaciens* strain LBA4404 Rif (A. Hoekema et al. (1983) *Nature* 303:209–213) for subsequent transfer into plant tissue.

Leaves of *Nicotiana tabacum* cv. Wisconsin 38 growing in tissue culture on Murishige and Skoog (MS) medium (T. Murishige and F. Skoog (1962) *Physiol. Plant.* 15:473–497) were cut into pieces (1 square cm) under liquid MS medium to prevent desiccation and added to a suspension of the transforming Agrobacterium strains. Bacteria were pre-grown on YM slopes (J. Ellis et al. (1979) *Physiol. Plant Pathol.* 15:311–319) and then resuspended in 10 ml each MS liquid medium. After 20 minutes the infected leaf pieces were transferred to MS agar and incubated for 24 h at 25° C. The leaf pieces were then washed in sterile water and transferred to MS9 shoot induction medium (MS medium, 0.5 mg indole acetic acid, 1.0 mg benzyl aminopyrine, 100 mg kanamycin sulfate, 500 mg cefotaxime per liter. When shoots were 1–2 cm high they were transferred to MS medium containing the same antibiotics. Plants that formed roots were maintained under kanamycin selection.

1.5 Assay of chloramphenicol acetyl transferase activity in transformed tobacco

The plant tissue used in the assay was either young leaves of transgenic plants or shoot cultures initiated from leaf pieces of transgenic plants on medium containing kanamycin sulfate. The plant material was made anaerobic by incubation at 28° C. on MS agar in an argon atmosphere; 18 hours was found to be sufficient for induction.

The assay was performed as described by Herrera-Estrella et al. (1983), *Nature* 303:209–213 except that the extraction buffer contained 0.1% cysteine-HCl and 0.1% ascorbic acid. Each μg of tissue was extracted with 1 μl of extraction buffer, and cleared by centrifugation. To 50 μl of supernatant, 0.2 uCi of 14C-chloramphenicol (Amersham) was added then made to 1 mM acetyl CoA and incubated at 37° C. for 30 min. The ethyl acetate extract of the reactions were concentrated by evaporation and then chromatographed on silica gel plates in chloroform-methanol (95:5). The gel plates were sprayed with fluor (0.4% PPO in 1-methyl-naphthalene) and autoradiographed for 16 hours at −80° C.

1.6 Introduction of recombinant DNA into maize protoplasts

The Zea mays c.v. Black Mexican Sweet XII-11 suspension cell line (P. Chourey and D. Zurawski (1981) *Theor.*

*Appl. Genet.* 59:341–344) was cultured in modified MS medium (C. Green and R. Phillips (1975) *Crop Sci.* 15:417–421) at 26° C. Protoplasts were isolated according to the protocol of I. Potrykus et al. (1979) *Theor. Appl. Genet.* 54:209–214, and prepared for electroporation as previously described (E. Howard et al. (1987) Planta). For electroporation 100 μg of plasmid DNA was mixed with 1 ml protoplasts (3×106/ml) in HEPES-buffered saline (10 mM HEPES, pH 7.2, 150 mM NaCl) containing 0.2M mannitol (M. Fromm et al. (1985), *Proc. Nat. Acad. Sci. USA* 82:5822–5828). The cells were subjected to a 45° C. heat shock for 5 min, incubated on ice 5 min, and then electroporated by a single 50 msec pulse at 250 V using a capacitor-discharge electroporation apparatus, on ice. Following an additional 10 min incubation on ice, the cells were diluted tenfold with PCM (Chourey and Zurawski, supra).

1.7 Transient expression assays of reporter gene activity

Following electroporation samples of the protoplasts were divided into two aliquots; one was incubated aerobically (20% oxygen, atmospheric conditions) and the other was incubated anaerobically (5% oxygen/95% nitrogen). In both cases incubation was in the dark at 26° C. for 20 hours. The cells in each aliquot were then collected by centrifugation, resuspended in 250 μl 10.25 Tris-Cl, pH 7.5, sonicated, and assayed for chloramphenicol acetyl transferase enzyme activity. Substrate and reaction products were extracted with ethyl acetate and separated by thin layer chromatography as described (C. Gorman et al. (1982) Mol. Cell. Biol. 2:1044–1051). The chromatograms were fluorographed and spots quantitated by liquid scintillation counting as previously described (Howard et al. (1987) supra).

Each plasmid construction was assayed in from two to five separate electroporation experiments. Because of the variation between protoplast preparations and the efficiency of electroporation, results were normalized to give a value of 1 for the anaerobic expression of padhCAT after subtraction of the nonspecific background products as measured using plasmid padhCAT (Howard et al. (1987) supra ).

1.8 Adh1 promoter-dependent expression of cat gene activity pAdcat1 contained the maize promoter sequences found between −1094 and +106 relative to the cap site, and pAdcat2 contained that maize promoter DNA from −140 to +106. If either of these two plasmids carried cis-acting regulatory sequences which could promote anaerobic gene expression in tobacco, then cat enzyme activity should increase after a period of anaerobic induction. None of 14 plants transformed with the pAdcat1-binary vector construct expressed anaerobiosis-dependent cat activity over the background level for tobacco. Similarly, none of 29 plants transformed with the pAdcat2 construct expressed any anaerobically induced cat activity. The conclusion was that the maize adh1 promoter activity cannot be detected in the dicot species *Nicotiana tabacum* using the cat reporter gene system.

When these constructs were tested in transient expression experiments in maize protoplasts, it was found that cat enzyme activity was readily detectable and anaerobically induced. Thus, it appears that the adh1 promoter sequences are sufficient for effecting transcription initiation in a homologous system. Since there was no activity in the heterologous tobacco system, the pAdcat1 and pAdcat2 vectors might be used as probes for transcription activating elements inserted 5' to the maize adh1 promoter sequences.

EXAMPLE 2

Activation of the maize adh1 promoter by an upstream element from the octopine synthase gene promoter In this example the cloning regimen which led to the discovery of the transcription-activating activity of the ocs 5' region is elaborated.

2.1 Cloning of the transcription activating element

Ti plasmid pTiAch5 (G. de Vos et al. (1981) *Plasmid* 6:249–253) was digested with EcoRI and BamHI to release a 2.53 kb fragment carrying the ocs 5' untranscribed region. The BamHI site is at position −116 with respect to the start of ocs transcription, and the fragment extends in the 5'-direction toward the EcoRI site. That fragment was inserted into EcoRI-BamHI-digested pUC8. The resulting chimera was linearized with PstI and ligated to PstI-cut pAdcat2 to generate pAdcat3. The ocs 5'-untranscribed region is inserted 5' to the −140 to +106 portion of the maize adh1 sequences.

2.2 Activation of maize adh1 promoter activity

A pAdcat3 construct was introduced into tobacco cells; regenerated transformed plant tissue was prepared and assayed as described in Example 1. In at least 6 of 9 plants tested, cat enzyme activity was induced by anaerobiosis. S1 mapping experiments confirmed that transcription was initiated at the normal cap site within the adh1 region. Therefore, it was concluded that one or more sequences found within the 5' flanking region of the ocs gene was able to activate transcription of the maize adh1 promoter in a tobacco host.

It is noted that there was considerable variation in the absolute levels of enzyme activity, and that some transgenic plants shown to carry the recombinant sequences by Southern hybridization experiments have no detectable activity (this work; J. Jones et al. (1986), supra. Therefore it is important to assay several transgenic plants for the desired recombinant phenotype; 20–30 are recommended for statistical validity.

EXAMPLE 3

Characterization of the transcription activating element

This example describes the steps taken to localize the transcription activating element within the 5' flanking region of the ocs gene. A 16 bp palindromic sequence 5'-ACGTAAGCGCTTACGT-3' was identified as sufficient to activate adh1-promoted transcription in the tobacco model system.

3.1 Localization of the transcription activating element to a 176 bp fragment pAdcat3 was cut with BamHI and HpaII, and the 176 bp fragment, which extends from −292 to −116 relative to the start of ocs transcription was purified and ligated with pBR322 which had been digested with BamHI and ClaI to yield pocs1. (pocs1 can serve as a source of element-containing DNA, and it can serve as a recipient vector into which to insert promoter/ foreign structural gene/polyadenylation signal complexes for subsequent manipulations.) The small EcoRI-BamHI fragment from pocs1 was inserted into pUC8 and then the PstI fragment of pAdcat1 inserted to give pAdcat5. pAdcat6 was constructed as follows: pocs1 DNA was cut with PstI and EcoRI and then treated with Klenow fragment and ligated to PstI linkers. After PstI digestion and removal of excess linkers, the PstI fragment of pAdcat1 was inserted. This fragment carried part of the amp gene and when inserted in the correct orientation, it complemented the deletion created in the amp gene of pOCS1 by the initial PstI-EcoRI digestion. This placed the ocs 5' region upstream of the adh1 promoter but in an inverted orientation with respect to pAdcat5. A HindIII linker was inserted at the SalI site of this plasmid to give pAdcat6 so that it could be ligated into the binary vector.

pAdcat5 and pAdcat6 derivatives were introduced into tobacco and those transformed plant tissues were assayed for anaerobically induced cat enzyme activity. 10 of 21 pAdcat5-transformed plants and 11 of 17 pAdcat6-transformed plants expressed inducible cat enzyme activity. Therefore the 176 bp fragment was capable of activating transcription from the maize adh1 promoter, and this activation was independent of the orientation of that fragment relative to the adh1 promoter region. Similar results were obtained with maize protoplasts into which these plasmids had been electroporated.

3.2 Analysis of sequence for potential regulatory regions

The published nucleotide sequence of the 5' untranscribed region of the ocs gene was analyzed for regions of potential secondary structure which might indicate sites of regulatory function. Computer analysis revealed two regions of dyad symmetry. A 16 bp palindrome (5'-ACGTAAGCGCTTACGT-3') was found at −194 to −179 and a 12 bp palindrome (5'-GATGTTAACATC-3') was found in the region −149 to −138. Experiments were then designed to test these two sequences for their role(s) in transcriptional activation.

3.3 Deletion analysis of the 176 bp fragment to identify and localize the active transcriptional activating element 5' and 3' deletions of the 176 bp HpaII-BamHI fragment were generated using Bal31 nuclease digestion after cutting with either HpaII (for 5' deletions) or BamHI (for 3' deletions). After treatment with S1 nuclease, the Klenow fragment of E. coli DNA polymerase I, ligation, and transformation, the ocs-derived fragments were excised, subcloned, and sequenced as described above to determine the deletion endpoints. Suitably deleted ocs-derived fragments were then ligated to padhCAT-100 for functional analysis. pAdCAT-100 was prepared from padhCAT-140, which contains −140 to +106 of the adh1 promoter, cat coding sequences, and the nos 3' polyadenylation signal in pUC19. padhCAT-140 was cut with SmaI, digested with Bal31 and fill-in repaired with the Klenow fragment of DNA polymerase I, and modified by the addition of a SalI linker. After SalI-HindIII digestion, fragment purification after low melting temperature agarose gel electrophoresis, subcloning into pUC19 and sequencing to determine endpoints, padhCAT-100 was constructed by subsequent subcloning of the adh1 region plasmid. Without the addition of a transcription activating element the padhCAT-100 has only background levels of reporter gene activity in either maize or tobacco protoplasts. The incorporation of the 176 bp HpaII-BamHI fragment of the ocs 5' region restores activity comparable to that observed with pAdCAT-140 in maize protoplasts.

The series of deleted plasmids were electroporated into both maize and tobacco protoplasts and assayed in the transient expression for activation of reported gene expression. The 5' deletions extending to −280 and −207 had full enhancer-like activity while the 5' deletion to −168 had only a small fraction of full activity. A 5' deletion ending at −159 had no activity. A set of 3' deletions were also analyzed for loss of transcription activation activity. 3' deletions extending from the BamHI site to −144, −157, and −178 all had essentially full activity. A 3' deletion to −203 allowed no expression of the reporter gene. Thus, the sets of deletion mutants defined a region of DNA between −207 and −178 which is required for the activation of downstream gene expression. It is within this region that the 16 bp palindromic sequence lies. There appeared to be a minor transcription activating activity between −168 and the BamHI site; the 12 bp palindromic sequence is within this portion of the ocs-derived fragment.

3.4 Synthesis and activity of the synthetic 16 bp palindromic sequence

The 16 bp palindromic sequence was chemically synthesized using an automated DNA synthesizer, Model 380A (Applied Biosystems, Foster City, Calif.). The actual sequence of the oligonucleotide which was inserted into padhCAT-100 is 5'-GGATCCACGTAAGCGCTTACGTGGATCC-3'. (It should be noted that the resultant palindrome extends a total of 28 bp.) The construct was electroporated into both maize and tobacco protoplasts and assayed for transcriptional activation in the transient expression system. The magnitude of the activation of cat activity was not significantly different than that observed with the HpaII-BamHI fragment derived from ocs. Similar results were obtained using or synthetic oligonucleotide with one BamHI and one EcoRI end, in a construction in which there was no extension of the palindrome. Therefore, when one considers the results from the deletion analysis and the results from the synthetic oligonucleotide, it appears that the primary component of the transcription activating element is within the 16 bp palindromic sequence 5'-ACGTAAGCGCTTACGT-3'.

3.5 Positional requirements for the transcription activating element

The 16 bp palindrome is located approximately 200 bp 5' to the transcription start site, or about 175 bp 5' to the TATA box in pAdcat5. The effects of increasing the distance between the transcription activating element and the cap site were tested with two novel constructs.

The small BamHI-SalI fragment of pBR322 was inserted between the ocs-derived fragment and the adh1-derived promoter fragment with the result that the distance between the palindrome and the cap site was increased to approximately 475 bp. There was an approximate loss of transcription activating ability of 25% at this distance from the signals for the initiation of transcription. A second construct contained a roughly 1200 bp fragment of Tn903 inserted between the ocs-derived and adh1-derived fragments; thus, the intervening distance in this case was about 1400 bp. Only a small fraction of the transcription activating activity was detectable at this distance.

Closer positioning of the palindromic sequence to the cap site of the adh1 promoter was achieved by fusing the ocs-derived fragment to a series of 5' deleted adh1 promoter fragments. The level of expression for padhCAT-99 (41 bp deleted) was comparable to that for padhCAT5. In this case the distance between the transcription activating element and the cap site was decreased from approximately 200 bp to about 160 bp. Fusion of the ocs-derived fragment to a 5' deletion of the adh1 promoter to −35 yielded padhCAT-35, wherein the distance between the cap site and the transcription activating element was reduced to about 95 bp. Transcription activation and regulation were maintained. When the TATA box of the adh1 promoter and the cap site were deleted, the ocs-derived fragment did not activate expression of the cat reporter gene, i.e., the ocs-derived fragment used in these experiments had no endogenous promoter activity.

EXAMPLE 4

This example describes the sequences homologous to the OCS element in other genes. These DNA fragments were tested for their ability to bind a nuclear protein factor (ocs factor) present in maize and tobacco nuclei.

Figure 5C:
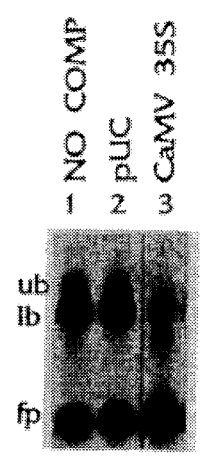

4.1 Presence of an active OCS element in the 35S promoter of the CaMV (a) Binding to the ocs factor A 31 bp fragment (−89 to −59) of the 35S promoter containing the sequence homologous to the OCS element was analyzed in a gel retardation assay with nuclear protein extract. The interaction between this fragment and the nuclear extract produced two retarded bands (FIG. 5b, Lane 1). The same pattern of retarded complexes is characteristic of gel retardation experiments involving fragments containing the 16 bp palindrome of the ocs promoter (Singh et al. (1989) supra). The binding to the 35S promoter fragment was competed by addition of DNA fragments containing the ocs 16 bp palindrome (FIG. 5b, Lanes 2 and 3). In controls, no competition was observed when the same amount of pUC19 polylinker DNA was used as a competitor (FIG. 5b, Lane 4). Conversely, the binding to ocs promoter fragments is competed by the 35S promoter fragment (FIG. 5c, Lane 3). These experiments indicate that the 31 bp fragment from the 35S promoter and the 16 bp palindrome from the ocs promoter interact with the same nuclear factor(s).

Figure 5D:
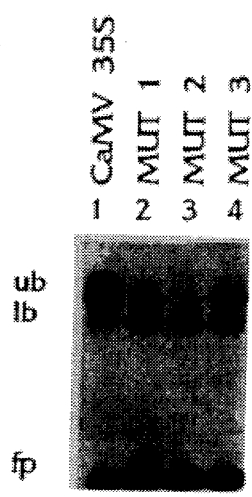

(b) Oligonucleotide directed mutagenesis of the OCS element in the CaMV 35S promoter To analyze the importance of this region on the transcriptional activity of the 35S promoter, three different sequence alterations were introduced by oligonucleotide directed mutagenesis (FIG. 5a). The effect of these changes on promoter activity was tested by transient expression assays in protoplasts. The first mutation changed the sequence TAAG between the two repeats of the pentanucleotide elements to CCTC, while the second one changed the ACG trinucleotide of the 5' repeat to TAT. The third mutation changed the sequence TG of the 5' pentanucleotide element to GA. Mutant 1 reduced the expression of a linked GUS reporter gene by 76% with respect to the wild-type level. Mutant 2 had the most dramatic effect on GUS activity, reducing it to background levels. Mutant 3 had wild-type activity. The effect of the mutations on protein binding was assayed by gel retardation. The −89 to −59 fragments of the wild-type promoter and the three mutants were analyzed (FIG. 5). Binding to mutant probes 1 and 3 was reduced (FIG. 5d, Lanes 2 and 4). No upper band was detected with the probe from mutant 2 (FIG. 5, Lane 3) which is the mutant with lowest promoter activity. A strong correlation between the presence of the upper band complex and enhancer activity has previously been observed with mutants of the 16 bp palindrome of the ocs gene (Singh et al. (1989) supra). It is unclear why the decreased binding to the Mutant 3 probe was not accompanied by an effect on transcription. From these experiments, it is evident that the 35S promoter contains a functional OCS element and that this element is essential for the activity of the promoter.

(c) Wound inducibility

The 35S promoter-CAT/NOS gene construct was tested for wound inducibility. The 35S promoter was deleted to −90 and comprised essentially of the OCS enhancer element and the TATA box. Such constructs showed a six-fold enhancement in level of expression in response to wounding.

(d) Wounding protocol

Leaves (4–5 cm) were removed from sterile transformed tissue culture plants. Each leaf was split in two along the mid-rib. One-half was extensively wounded with a scalpel blade. Each half was placed in a separate petri plate on 2% water agar for 16–20 hr. Cat assays were then performed and the results from each leaf half compared.

4.2 OCS elements in the genes for mannopine and agropine synthesis on the T-DNA of Ri and Ti plasmids The agropine family of opines is synthesized by enzymes encoded by genes located on the T-DNA of octopine Ti plasmids and agropine Ri plasmids. Three genes are involved in agropine biosynthesis on the T-DNA of octopine Ti plasmids (Ellis et al. (1984) *Mol. Gen. Genet.* 195:466–473). The first two enzymes in the pathway, leading to mannopine formation, are encoded by the 2' and 1' genes which are divergently transcribed and herein are referred to as MAS2' and MAS1'. The third enzyme in the pathway is encoded by the 0' transcript and converts mannopine to its cyclic form, agropine; this gene is referred to as the agropine synthase or ags gene. The same biosynthetic pathway is encoded by agropine type Ti plasmids (Petit et al. (1983), and the same genetic arrangement occurs. However, the homology between the genes is restricted to the coding regions.

Figure 6B:
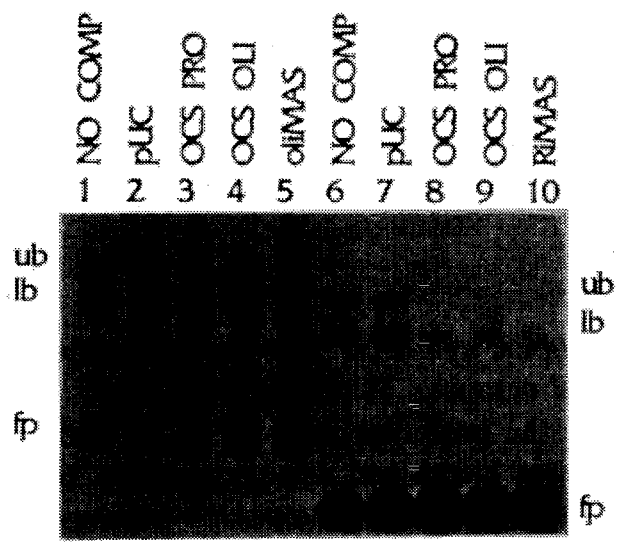
FIGS. 6a–6b. The RiMAS OCS element. Sequence of the oligonucleotide, oliMAS, containing the 16 bp region of the RiMAS element (bold type) homologous to the ocs promoter. The restriction sites indicated by single or double letter abbreviations correspond to the polylinker sites in pUC18. (a) gel retardation of DNA fragments containing the RiMAS element, either a 125 bp ApaI-Sau3AI fragment from the promoter region (lanes 1–5) or a fragment containing a.cloned synthetic RiMAS 16 bp element oliMAS (lanes 6–10). Various fragments were tested for their ability to compete the Binding of probes: DNA containing the ocs palindrome, either from the ocs promoter (lanes 3 and 8) or from a cloned synthetic palindrome (lanes 4 and 9), the cloned MAS oligonucleotide (lane 5), and the 125 bp fragment from the Ri promoter (lane 10). No competition is observed with the polylinker of pUC (Lanes 2 and 7). (b) a cloned synthetic ocs palindrome was used as a probe in gel retardation (lane 1). Competition experiments with the pUC polylinker (lane 2) or the 125 bp Ri fragment (lane 3) are shown. Abbreviations are as in FIG. 2.
Figure 6C:
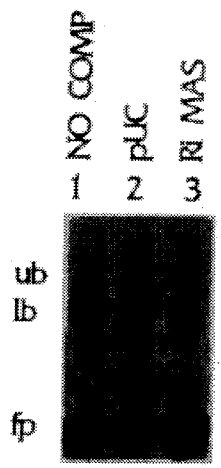

(a) Presence of OCS elements in the mannopine synthase gene on the T-DNA of Ri plasmids A sequence homologous to the ocs 16 bp palindrome ($^{13}/_{16}$) occurs approximately equidistant between the divergently transcribed MAS2' and MAS1' genes on the T-DNA of pRiA4. A 125 bp fragment containing this sequence bound to the ocs factor, giving a typical two-band pattern (FIG. 6a, Lane 1). Binding to this fragment was competed by an unlabelled fragment containing the ocs 16 bp palindrome (FIG. 6a, Lanes 3 and 4) and conversely, this fragment competed with the binding of the ocs factor to the ocs palindrome (FIG. 6b, Lane 3). A fragment containing a 16 bp oligonucleotide corresponding to the region homologous to the ocs palindrome competed the binding to the 125 bp fragment (FIG. 6a, Lane 5). As a probe, this fragment also gave a double-band binding (FIG. 6a, Lane 6) which was competed by DNA fragments containing the ocs palindrome and by the 125 bp fragment of the MAS promoters (FIG. 6, Lanes 8, 9 and 10). The importance of this region of the Ri-plasmid for activity of the divergent MAS1' and MAS2' promoters was indicated by expression studies in plant tumor cells: 5' deletion analysis of the MAS2' promoter showed that a 70 bp region containing this element is essential for activity, giving a 10-fold decrease in promoter expression when deleted and similar results were obtained with the MAS1' promoter, showing that the same region is involved in the activity of both promoters. These promoters therefore share a common element that binds the ocs factor and this element occurs in a region that is important for the function of the promoters.

Figure 7A:
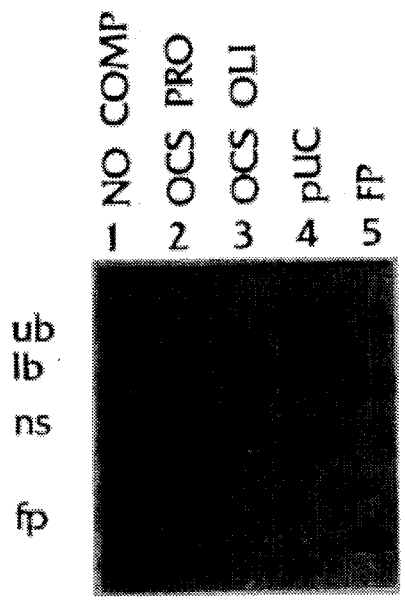
FIGS. 7a–7c. Gel retardation assays using the OCS element of the MAS1' and MAS2' genes of Ti plasmids. (a) MAS1' probe with no DNA competitor fragment (lane 1), ocs promoter competitor (lane 2), ocs 16 bp palindrome competitor (lane 3), pUC polylinker competitor (lane 4). (b) MAS 2' probe (c) ocs palindrome probe with no competitor (lane 1), pUC polylinker competitor (lane 2), Ti MAS1' fragment (lane 3) and Ti MAS2' fragment (lane 4). Abbreviations are as in FIG. 2.
Figure 7B:
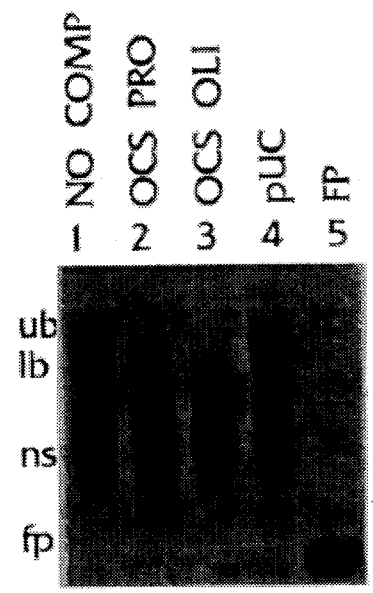
Figure 7C:
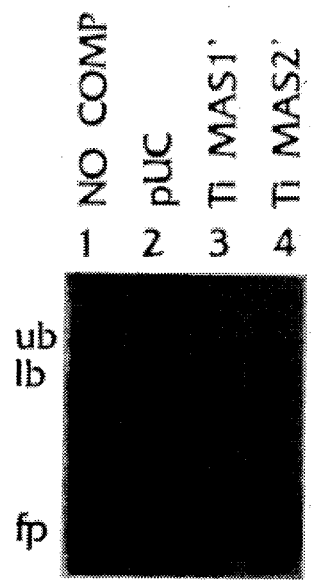

(b) Presence of OCS elements in the mannopine synthase gene on the T-DNA of Ti plasmids The arrangement of the sequences homologous to the OCS element in the divergent mannopine synthase genes on the T-DNA of the octopine type Ti plasmid pTiAch5 is different from the Ri plasmid: two elements occur in the promoter region of these genes. The MAS1' and MAS2' sequences are identical to the 16 bp palindrome of the ocs promoter at 9 out of 16 bases and 10 out of 16 bases, respectively and occur within 40 bases of the TATA boxes (FIG. 4). DNA fragments containing the two regions of homology were isolated and used as probes or binding competitors in gel retardation experiments. Both fragments competed with the binding of the ocs 16 bp palindrome to the ocs factor (FIG. 7c, Lanes 3 and 4) and gave two retarded bands (FIGS. 7a and 7b, Lane 1). Binding was competed by fragments containing the ocs palindrome (FIGS. 7a and 7b, Lanes 2 and 3).

Figure 8B:
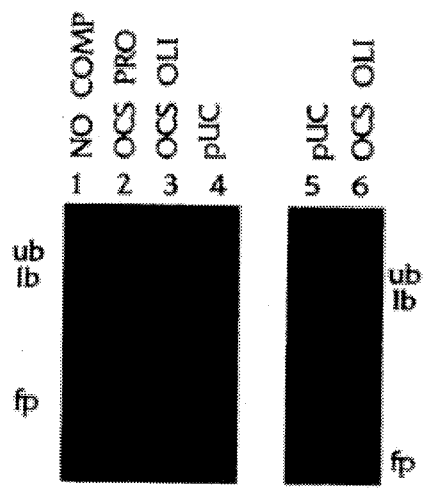
Figure 8C:
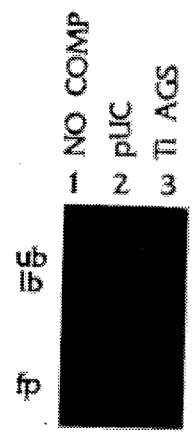

(c) Presence of OCS element in the agropine synthase gene on the T-DNA of Ti plasmids The element contained in the ags gene was studied in more detail for both binding to the ocs factor and in vivo activity because it was interesting to test whether the low sequence similarity (50%) with the palindrome of the ocs promoter could have a functional significance. A 64 bp fragment containing this region of the ags promoter and a synthetic 19-mer oligonucleotide comprising this site, competed the binding of the ocs factor to the 16 bp palindrome of the ocs promoter and both ags promoter probes bound specifically to the ocs factor (FIG. 8).

Figure 8D:
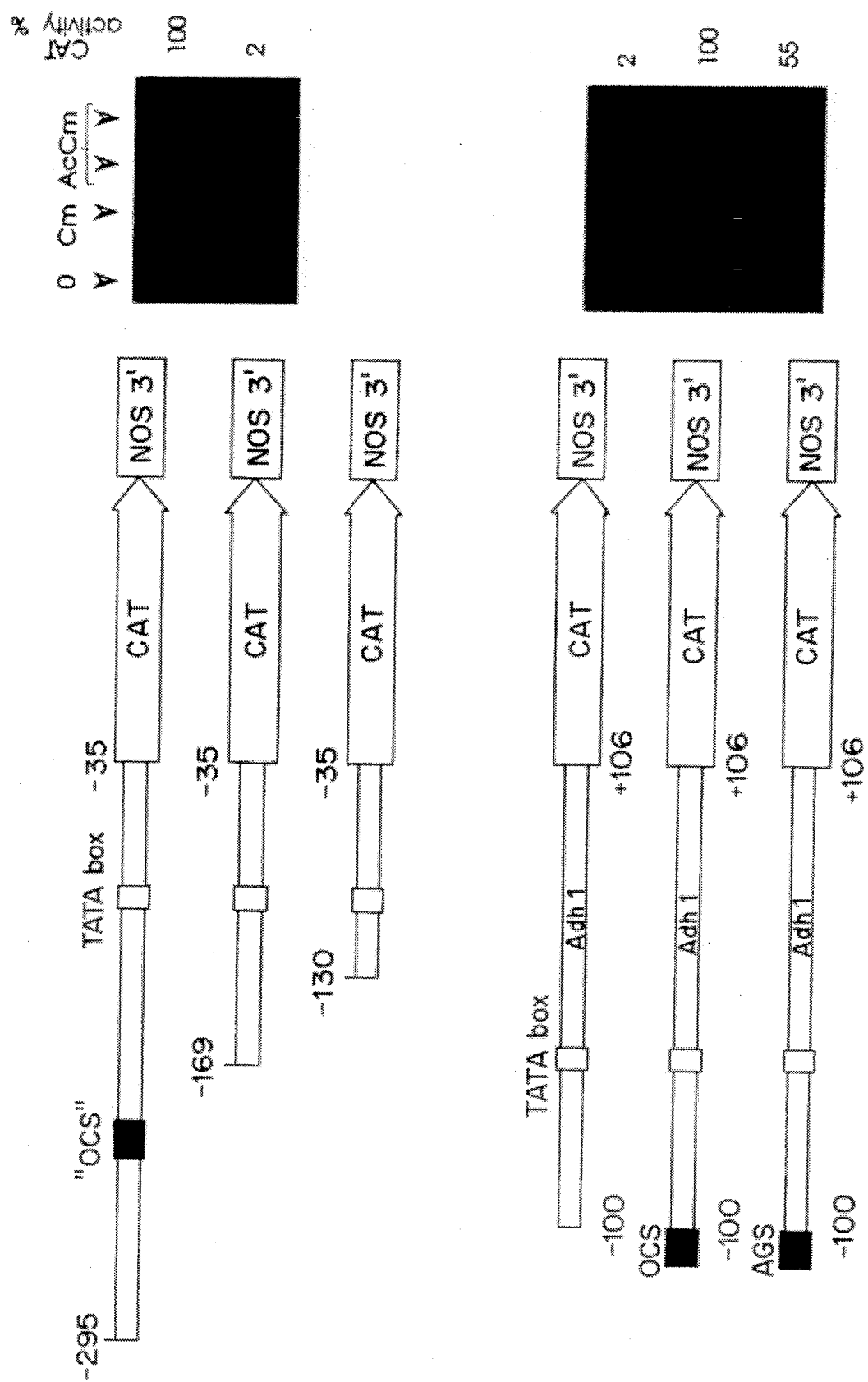

Two 5'-deletion mutants of the ags promoter, linked to a CAT-NOS3' cassette were tested for transient expression in plant protoplasts. The 5' end-points of the deletions were −295 and −169. While the −295 deletion gave high expression, the −169 promoter gave background levels, showing the presence of an essential promoter element in the −295 and −169 region (FIG. 8d); the OCS element is located at position −209 to −194. Furthermore, when the ags synthetic oligonucleotide was inserted in front of an inactive mutant of the maize adhI promoter linked to a CAT-NOS3' reporter cassette, transient expression analysis revealed that this sequence enhances the expression of the reporter gene (FIG. 8d).

It is therefore clear that, despite the low homology observed, the promoter for the agropine synthase gene of pTiAch5 contains a functional OCS element that interacts specifically with the ocs nuclear factor in vitro and that activates the transcription of an inactive promoter in vivo.

4.3 An OCS element in the nopaline synthase promoter

Figure 9B:
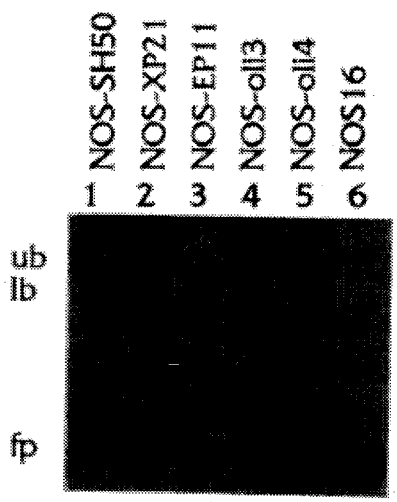
Figure 9C:
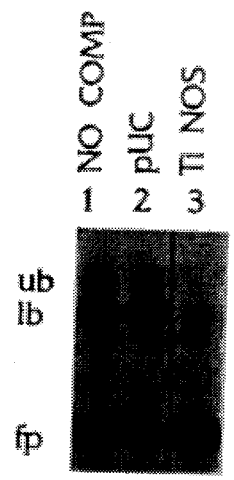

The nos promoter contains a sequence that matches the ocs 16 bp palindrome at 12 out of 16 sites but a synthetic copy of this sequence had no enhancer activity when linked to an inactive adh1 promoter (Ellis et al. (1987) *EMBO J.* 6:3203–3208). When this sequence was excised from pNOS16, the DNA fragment neither bound to a nuclear protein (FIG. 9b, Lane 6) nor competed with the binding of the ocs factor to the 16 bp palindrome of the ocs promoter. However, when a larger 50 bp fragment (−149 to −97) of the nos promoter that contains this region was used as a probe, a two band retardation pattern resulted (FIG. 9b, Lane 1). The same fragment competed the binding of the ocs factor for the 16 bp palindrome of the ocs promoter (FIG. 9c, Lane 3). In addition, binding of the 50 bp nos promoter fragment was competed by DNA containing the 16 bp palindrome. These experiments clearly demonstrate that the NOS promoter and the ocs promoter interact with the same nuclear factor. In the case of the nos promoter however, the 16 bp region that is homologous to the ocs promoter is not sufficient for binding. Therefore, to precisely define the extent of the nos promoter sequence needed to give a double band binding pattern, several restriction fragments and synthetic oligonucleotides containing smaller fragments of the nos promoter were used as probes and competitors of binding in gel retardation experiments. The fragment from pNOS-XP21 (FIG. 9a) contained the nos promoter sequence from −129 to −97 and the fragment from pNOS-EP11 (FIG. 9a) contained sequences from −127 to −97. Deletion of the sequences between −149 and −129 resulted in a major reduction in the upper band (FIG. 9b, Lane 2). Deletion of the sequences between −149 and −127 eliminated the upper band but the lower band was retained (FIG. 9b, Lane 3). Both fragments competed with binding of an ocs promoter probe to the ocs factor.

The smallest fragment of the nos promoter that was examined and that competed with the interaction between the ocs factor and the ocs promoter and that gave lower band binding in gel retardation (FIG. 9b, Lane 4) was derived from pNOS-oli3 (FIG. 9a) which contained 19 bp of nos promoter (−130 to −112). This extended the 16 bp in pNOS16 by 2 bp at the 3' end and by 1 bp on the 5' side. When a fragment from pNOS-oli4 (FIG. 9a) which contained one more base on the 5' side and contained 20 bp of nos promoter sequence (−131 to −112) was used as a probe, there was a double band binding pattern equivalent to that observed with the 50 bp probe of pNOS-SH50 (FIG. 9b, Lane 5).

Figure 9D:
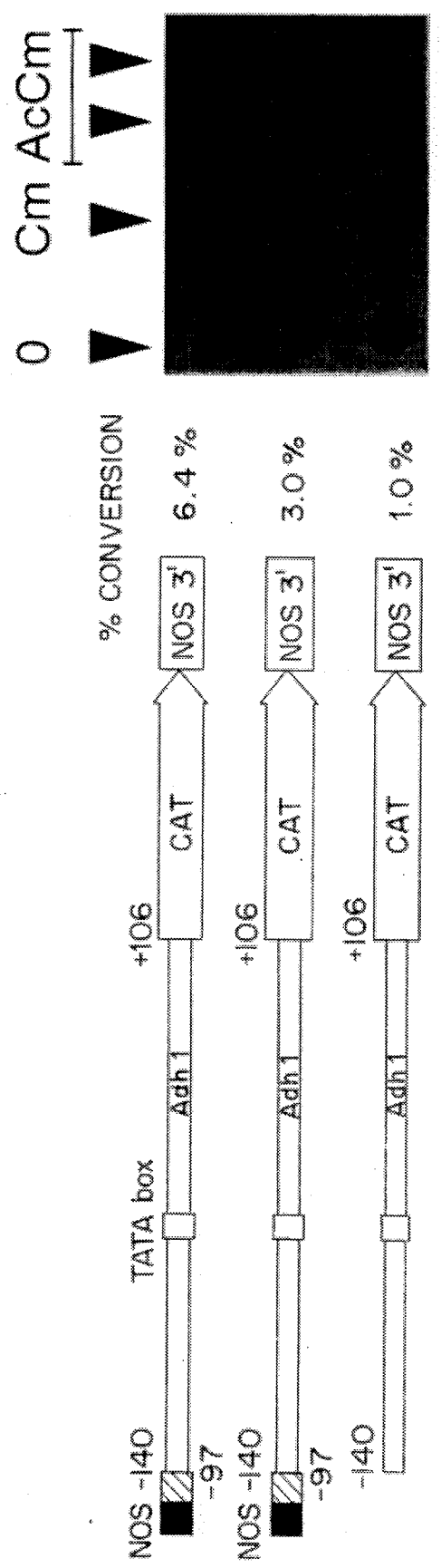

The importance of the DNA sequences in this region for the nos promoter activity has been demonstrated by deletion analysis of the nos promoter (An et al. (1986) *Mol. Gen. Genet.* 203:245–250; Ebert et al. (1987) *Proc. Natl. Acad. Sci.* 84:5745–5749; Mitro and An (1989) *Mol. Gen. Genet.* 215:294–299). Sequences from the nos promoter (−149 to −97 and −129 to −97) were compared to the sequence from the ocs promoter (−206 to −171) which contains the 16 bp palindrome, for ability to enhance the inactive adh1 promoter (see Ellis et al. (1987) *EMBO J.* 6:3203–3208). The nos sequences between −149 and −97 and between −129 and −97 had 51% and 24% of the enhancing activity of the OCS enhancer (FIG. 9d). The difference in enhancement by the ocs promoter fragment and the 50 bp nos promoter fragment may reflect differences in in vivo affinity of the two sequences for the ocs factor, spacing differences between the OCS element and the TATA box or both.

4.4 Recombinant DNA techniques and gene constructs

Recombinant plasmids were constructed using standard techniques described in Maniatis et al. (1982) supra). Site-directed mutagenesis by oligonucleotides was performed according to Kunkel (1985) *Proc. Natl. Acad. Sci.* 82:488–492. All oligonucleotides were synthesized using an Applied Biosystems 380A DNA synthesizer. Single stranded oligonucleotides were cloned using the method of Derbyshire et al. (1986) *Gene* 46:145–152, or both strands were synthesized, annealed and cloned as described in Ellis et al. (1987) *EMBO J.* 6:3203–3208. For expression analysis, synthetic oligonucleotides and promoter fragments were cloned 5' of the −100 adh-cat-nos 3' cassette of pACN-100 (Ellis et al. (1987) *EMBO J.* 6:3203–3208) or in the case of the nos promoter fragments, the −140 adh-cat-nos 3' cassette of pAdcat2 (Ellis et al. (1987) *EMBO J.* 6:11–16). The ags promoter vectors contained DNA from the AccI site at −35 to the HaeIII site at −169 or the AccI site at −295. These coordinates are with respect to the A residue of the translation initiation codon. The transcript start has not been mapped. The 35S-GUS-nos 3' expression plasmid used for mutagenesis was kindly provided by Dr. John Walker (University of Missouri).

4.5 Gel retardation assays

Nuclear protein extracts from maize cell suspension cultures were prepared according to Green et al. (1987) *EMBO J.* 6:2543–2549. The binding reactions typically contained 5000 cpm of the end-labelled probe (0.05–0.2 ng), 1.0 μg of poly(dI-dC), 5 μg of crude nuclear extract in binding buffer (25 mM HEPES, 50 mM KCl, 1 mM EDTA, 10% glycerol, 5 mM 2-mercaptoethanol) and the gel retardation was performed as described by Garner and Revzin (1981) *Nucl. Acids Res.* 9:3047–3060 and Fried and Crothers (1981) *Nucl. Acids Res.* 9:6506–6525. Competitor DNA was added to the reaction in 100–300-fold molar excess.

Fragments used for probes and competitors in gel retardation were eluted from 10% acrylamide gels. Probes were end-labelled using Klenow enzyme and $dCT^{32}p$. The ocs promoter fragment was either excised with EcoRI and HindIII as a 52 bp fragment from pUC19pal16 (Ellis et al. (1987) *EMBO J.* 6:3203–3208) which contained a cloned synthetic copy of the 16 bp palindrome or excised as a 48 bp fragment with XhoI and PstI from a pUC8 clone. This fragment contained bases −206 to −171 (XhoI to TaqI of Del5'206, Ellis et al. (1987) *EMBO J.* 6:3203–3208. The 31 bp fragment of the 35S promoter was excised with EcoRV (−89) and Fok1 (−59). The 125 bp fragment of the Ri MAS promoters was excised from a larger clone of the promoter region with ApaI and Sau3A1. A smaller fragment of this promoter was derived from a synthetic 16 bp oligonucleotide (FIG. 6) cloned in pUC118 and excised as a 60 bp fragment with EcoRI and HindIII. The MAS1' and MAS2' promoter fragments of the Ti-plasmid were excised from pKU2 (Baker et al. (1987) *EMBO J.* 6:1547–1554). The Mas2' fragment (137 bp) was excised from the promoter using ClaI and HinP1. The MAS1' fragment (145 bp) was excised from the promoter with HaeIII, cloned into the SmaI site of pUC118 then reisolated as a BamHI-EcoRI fragment. The ags promoter fragment (64 bp) was excised from a larger fragment (EcoRI fragment 20, Ellis et al. (1984) *Mol. Gen. Genet.* 195:466–473) of the T-region of pTiAch5 with HaeIII and AluI, cloned into pUC118 and reisolated as an 86 bp EcoRI-BamHI fragment. A fragment (54 bp) containing a 19 bp synthetic copy of the OCS element of the ags gene was excised from pUC19 with EcoRI and HindIII. The nos promoter fragments were isolated from the T-DNA gene or from pUC19 containing various synthetic copies of the nos promoter region (pNOS-oli3, pNOS-oli4 and pNOS16). pNOS-SH50 contained the SacII (−149) to HinPI (−97) fragment of the nos. promoter. pNOSXP21 contained the AluI (−127) to PstI fragment of pNOS-SH50 cloned into the PstI and filled XbaI sites of pUC19. pNOS-EPl1 contained the same fragment cloned into the PstI and filled EcoRI site of pUC19.

4.6 Transient expression analysis

*Nicotiana plumbaginifolia* protoplasts were isolated from the cell suspension culture NpT5 as previously described (Llewellyn et al. (1987) *J. Mol. Biol.* 195:115–123). Protoplasts were electroporated using 10 μg of plasmid DNA. After 24 hour incubation at 25° C., they were lysed by sonication and the protein concentration in the extracts was measured.

CAT activity was assayed as previously described (Llewellyn et al. (1987) supra). The conversion of $^{14}C$ chloramphenicol to acetylated chloramphenicol was determined by cutting the substrate and acetylated product from TLC plates and counting by liquid scintillation. GUS activity was measured according to Jefferson (1987) *EMBO J.* 6:3901–3907 using the fluorogenic substrate 4-methyl umbelliferyl glucuronide.

EXAMPLE 5

This example describes binding between the OCS element DNA and an ocs transcription factor isolated from maize nuclear extract. The consensus nucleotide sequence of the OCS element was tested for the presence of recognition sites capable of binding the ocs transcription factor.

5.1: The preparation of DNA fragments for gel retardation and footprint analyses (a) Gel retardation: Two DNA fragments for gel retardation were from the promoter of the ocs gene: a 58-bp XhoI-HpaI fragment containing the element and flanking sequence from the plasmid pΔ5'-206 corresponds to −206 to −143 relative to the transcription start site; a 52-bp XhoI-SalI fragment from the plasmid pΔ5'-157 corresponds to −157 to −116 (Ellis et al. (1987) *EMBO J.* 6:3203–3208). The 54-bp, PstI-SalI DNA fragment from plasmid pLSPstI-89/−80 contains the anaerobic regulatory element of alcohol dehydrogenase I (Walker et al. (1987) *Proc. Natl. Acad. Sci.* 84:6624–6628). The nonspecific competitor was an 80-bp, HaeIII-HaeIII fragment from the plasmid pUC18. The PvuII-SalI fragment (123 bp) containing either the 16-bp wild-type or various mutated OCS elements was from plasmid gene constructs described by Singh et al. (1989) supra.

(b) Footprint: The HindIII-SalI fragment containing the wild-type or mutated OCS elements (Singh et al. (1989) supra) was filled in at the HindIII site with the Klenow fragment of DNA polymerase I, cloned into the SmaI-SalI polylinker site of pUC118 and used as an EcoRI-HindIII fragment (67 bp).

5.2: The preparation of $^{32}P$-labelled DNA fragments and markers for gel retardation and footprint analyses Fragments for gel retardation were isolated from polyacrylamide gels and incubated with the Klenow fragment of DNA polymerase I and nucleotide triphosphates in which an incorporated nucleotide was $^{21}$P-labelled. The reaction was terminated by the addition of ammonium acetate to a final concentration of 2M and the DNA recovered by ethanol precipitation. The DNA concentration was adjusted to 5,000 cpm (Cerenkov)/μl (0.1–0.5 ng/μl). for footprint analyses, DNA fragments were labelled on either the top or bottom strand by restriction of the plasmids with either HindIII or EcoRI followed by heat inactivation, incubation with the Klenow fragment of DNA polymerase I and nucleotide triphosphates with one of the incorporated nucleotides $^{32}$P-labelled followed by heat inactivation, incubation with the complementary restriction enzyme and isolation of the fragment from polyacrylamide gels followed by ethanol precipitation. The DNA concentration was adjusted to 100,000 cpm (Cerenkov)/μl. The adenine-guanine positions in the DNA fragments were identified by specific base reactions described by Maxam and Gilbert (1980) supra.

5.3: Generation of nuclear protein extracts from maize cell suspension cultures Protoplasts were prepared as described (Potrykus et al. (1979) *Theor. Appl. Genet.* 54:209–214) from a Zea mays c.v. Black Mexican Sweet XII-II suspension cell line (Chourey and Zurawski (1981) *Theor. Appl. Genet.* 59:341–344; generously provided by P. Choury, Florida State University). Nuclei were isolated essentially by method II of Luthe and Quatrano (1980) *Plant Physiol.* 65:305–308. Nuclear protein extracts were prepared as described by Parker and Topol (1984) *Cell* 36:357–369. The final protein concentration was 1–3 μg/μl as determined by Bradford (1976) *Anal. Biochem.* 72:248–254 using bovine serum albumin as a standard.

5.4: Fractionation of protein-DNA mixtures

Gel retardation assays were as described previously (Garner and Revzin (1981) *Nucl. Acids Res.* 9:3047–3059; Fried and Crothers (1981) *Nucl. Acids Res.* 11:141–1158). For analytical assays, 3 to 10 μg of nuclear protein extract (stored at 1–3 μg/μl at −80°) was incubated with 0.1–1.5 μg of [poly(dI-dC)-poly(dI-dC)] and DNA at 5,000 cpm per reaction, adjusted to a final volume of 10 to 20 μl with *Nuclear Binding Buffer:* 10% glycerol., 25 mM HEPES (pH 7.8), 50 mM KCl, 1 mM EDTA, 5 mM 2-mercaptoethanol, and incubated at 30° for 30 minutes. The mixtures were fractionated on 4% acrylamide gels containing 22 mM Tris-borate (pH 8.0) and 0.5 mM EDTA with water cooling and buffer recirculation at 4° for 1.5 hours.

5.5: Methidiumpropyl-EDTA.Fe(II) reactions

Reaction conditions were established according to Van Dyke and Dervan (1983) *Nucl. Acids. Res.* 11:5555–5567. Preparative binding reactions (30 μl) containing 25 μg of nuclear protein extract, 4 μg of [poly(dI-dC)-poly(dI-dC)] and 400,000 cpm (Cerenkov) of $^{32}$P-labelled DNA fragments were incubated for 30 minutes at 30°, cooled to 25°, adjusted to a final concentration of dithiothreitol at 10 mM and methidium propyl-EDTA.Fe(II) (MPE) (the MPE was synthesized and purified as described by Hertzberg and Dervan (1982) *J. Am. Chem. Soc.* 104:313–315) at 0.001 to 0.01 mM, and incubated for 15 minutes at 25° to effect DNA cleavage. The mixture was incubated at 4° to inhibit the cleavage reaction and subjected to gel retardation as above with water cooling at −10°. Radioactive regions of the gel, identified by autoradiography of the wet gel for 2 hours at 4°, were excised and the DNA eluted with 500 mM ammonium acetate, 1 mM EDTA and 10 mM magnesium acetate. The DNA fragments in the eluate were mixed with 7 μg tRNA, recovered by ethanol precipitation and fractionated on an 8% sequencing gel.

5.6: Reconstruction of the upper band protein-DNA complex from the lower band complex Preparative binding reactions (20 μl) containing 16 μg of nuclear protein extract, 7.5 μg of l[poly(dI-dC)-poly (dI-dC)] and 300,000 cpm (Cerenkov, 6 ng DNA) of the PvuII-SalI fragment containing the mutated OCS element 6.1 were prepared and fractionated as described above for gel retardation. The protein-DNA complex that comigrated with the lower band complex of the wild-type element probe, was identified by wet gel autoradiography as described above, excised as a gel piece and the protein-DNA complex electroeluted into 22 mMTris-borate (pH 8.0), 0.5 mM EDTA, 5 mM 2-mercaptoethanol, 0.2 mM phenylmethylsulfonyl fluoride and 5 μg/ml bovine serum albumin at 4°. The eluate was concentrated by centrifugal microconcentrators (30 kDa cutoff, Centricon-30, Amicon Scientific, Australia) and adjusted to a final concentration of 1M NaCl. The eluate was diluted 10-fold with 10 mM Tris, 5 mM $MgCl_2$, 1 mM 2-mercaptoethanol after the addition of 10 units (Pharmacia) of HindIII and 30,000 cpm (Cerenkov) of the EcoRI-HindIII DNA fragment containing the wild-type OCS element. The eluate was incubated for 1 hour at 30°, concentrated by centrifugal microconcentration into Nuclear Binding Buffer. Gel retardation of the concentrate was as above.

5.7: Specificity of the protein-OCS element interaction

Figure 10A:
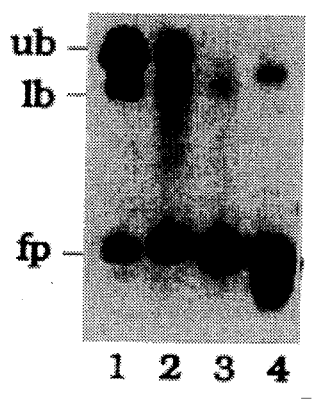
FIGS. 10a–10b. Gel retardation analysis for binding activity specific to the OCS element.

A crude extract was prepared from a nuclear fraction of cell suspension culture of maize and assayed, by gel retardation analysis, for DNA-binding activity specific to the OCS element (Garner and Revzin (1981) supra; Fried and Crothers, (1981) supra). As shown in FIG. 10A, the extract contained a binding activity which formed two retarded bands with each of two different $^{32}$P-labelled DNA fragments containing the OCS element (lanes 1, 2). In contrast, probes which lacked the palindrome sequence did not produce this same pattern (lanes 3, 4). Treatment of the extract with trypsin or proteinase K prior to the binding reaction eliminated the formation of retarded bands.

Figure 10B:
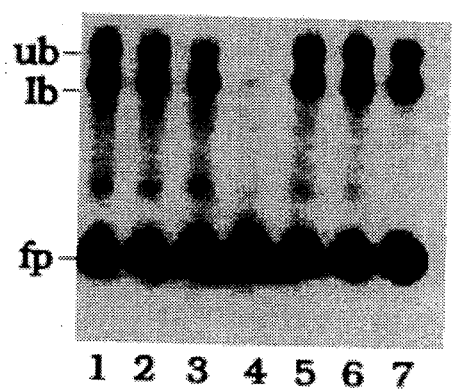

A similar pattern of two bands was obtained with nuclear protein extracts from *Nicotiana plumbaginifolia* cell suspension cultures (Singh et al. (1989) supra) as well as from extracts prepared from etiolated maize root and shoot tissue samples. Specificity of the binding activity was confirmed with the use of unlabelled competitor DNA which either contained or lacked the 16-bp palindrome. Competitor DNA containing the palindrome, when mixed with $^{32}$P-labelled DNA prior to the binding reaction, competed for the binding activity generating both the lower and upper retarded bands. FIG. 10B shows that a 50-fold molar excess competed almost all of the upper band and some of the lower band in the reactions (lane 3); a 500-fold molar excess competed all binding activity (lane 4). Similar concentrations of DNA lacking the palindrome were not effective competitors (lanes 5–7). These experiments showed that both retarded bands are formed by nuclear protein binding specifically to the OCS element sequence.

5.8: Relation of the two protein-DNA complexes

The observation of two retarded bands raised the possibility that different proteins bind to the OCS element, and/or that the element has more than one protein-binding site. The proportions of the two retarded bands were altered by varying the concentration of nuclear protein extract and carrier DNA in the binding reactions. As shown in FIG. 11A, the lower retarded band predominates with low extract concentration or with high carrier DNA concentration (lane 1), whereas the upper retarded band is dominant at higher extract concentrations in the presence of low concentrations of carrier DNA (lane 6). The relation between the two protein-DNA complexes was further investigated with mutated OCS elements as both probes and competitors in gel retardation assays. Singh et al. (1989) supra generated mutants of the OCS element which contained multiple base substitutions confined to one or other half of the palindrome sequence. As shown in Table 1 and FIG. 11B, mutants 3.3 and 6.1, which had base substitutions confined to the 5' or 3' palindrome halves, respectively, showed only one retarded band under reaction conditions in which a wild-type element formed both bands (Table 1; FIG. 11B, lanes 2, 3). Singh et al. (1989) supra had shown these mutated elements had low transcriptional enhancing activity. The single retarded band formed by these two mutants comigrated with the lower of the two retarded bands of the wild-type probe. When these mutated elements were used as competitors in gel retardation assays they competed lower and upper band complexes formed by wild-type and mutated elements (Table 1).

TABLE 1

Activity of OCS elements in gel retardation as probes and as competitors of binding activity

| OCS element | Probe Bands Generated | | Probe Bands Competed | |
|---|---|---|---|---|
| | Lower | Upper | Lower | Upper |
| Wild-type ACGTAAGC:GCTTACGT | + | + | – + | + |
| Mut 3.3 AAGCAAGG:GCTTACGT | + | – | + | + |
| Mut 6.1 ACGTAAGC:TTGCATGC | + | – | + | + |
| Mut 5.1 GCGACTGC:GCTTTCGT | – | – | – | – |

The ability of OCS elements with base substitutions concentrated in either one of the halves of the palindrome to form lower but not upper band indicates that upper band formation is sensitive to DNA sequence alterations and therefore is dependent on protein-DNA interactions. Further, the ability of these mutated elements to compete both bands of the wild-type element indicates that the two binding sites in the OCS element are identical. Comigration of the lower bands generated by wild-type or mutated elements confirms that similar or identical proteins bind to each of the two sites.

The possibility that the same binding protein is involved in the formation of both the lower and upper band complexes was tested directly in a gel retardation experiment where protein isolated from a lower band complex was shown to be sufficient to form both complexes in a reconstruction experiment. The mutated element 6.1 was used as the initial probe for the isolation of the lower band complex. This mutant sequence contains a HindIII restriction site (Table 1). Treatment of the probe with HindIII prior to a binding reaction abolished formation of the lower band complex, showing that HindIII cleavage inactivated the binding site.

The lower band complex formed with the 6.1 probe was recovered from gels by electroelution. Gel retardation analysis of the eluate showed that lower band complex and dissociated free probe (FIG. 11C, lane 2). The restriction enzyme HindIII was added to the eluate to reduce the number of protein binding sites contributed by the mutated element. Labelled wild-type OCS element which lacks a HindIII recognition sequence was added to provide an intact element for a binding reaction. The mixture was treated briefly with 1M NaCl to dissociate existing protein-DNA interactions and salt concentrations were adjusted for restriction enzyme activity and for the binding reaction. Electrophoretic analysis of this mixture showed the cut and uncut mutated element and intact wild-type OCS element (lane 3) and two bands that comigrated with the upper and lower bands of the wild-type OCS element (lanes 4, 5).

The possibility that a free protein comigrating with the lower band had been extracted and bound to the wild-type probe to form the upper band complex, was eliminated by a control experiment in which protein extract fractionated by gel electrophoresis in the absence of the OCS element was electroeluted and processed as described above. Fractionation of this mixture showed no protein-DNA complexes (FIG. 11C, lane 6).

5.9: Footprint analyses of the protein-DNA complexes

Results obtained with the mutated OCS elements and the data from the reconstruction experiment, indicate that the lower band protein-DNA complex is formed by one protein unit bound to one site of the OCS element whereas the upper band complex is formed by two protein units bound one to each of the two sites of the OCS element. This was confirmed by subjecting the DNA from the upper and lower bands to nucleotide protection analysis using methidium-propyl-EDTA.FE(II) (MPE), MPE being a reagent causing single-stranded cleavage of exposed DNA in solution (Van Dyke and Dervan (1983) supra. MPE was used in preference to DNase I because of its more random cleavage of the OCS element. A preparative-scale binding reaction was treated briefly with MPE and fractionated under nondenaturing conditions. The DNA was then extracted from both retarded bands and refractionated under denaturing conditions on an acrylamide gel.

Bottom strand DNA from the upper band complex (FIG. 12A, lane 6; FIG. 12C) was protected from bases 1–22, with more complete protection from bases 1–11. A similar pattern of protection was obtained with the top strand DNA from the upper band complex (FIG. 12B, lane 6; FIG. 12C); in addition, there was one partially unprotected base, 9. These data indicate that protein binds to the entire element, but more avidly to the 5' than to the 3' half of the element. Preferential binding of protein to the 5' half of the element is also indicated by the protection pattern of DNA from the lower band complex. Bottom strand DNA from the lower band complex was protected only in the 5' half of the element from bases 1–12 with more complete protection from bases 1–8 (FIG. 12A, lane 5; FIG. 12C). Top strand DNA was also protected from bases 2–14 (FIG. 12B, lane 5; FIG. 12C).

The lower band complex of the wild-type element consisted of protein bound to only the 5' half of the element, but with the mutant 3.3, in which the 5' binding site is altered by 3 base substitutions, footprint analysis of the lower band complex revealed protection only of the 3' half of the element. The bottom strand DNA (FIG. 13A, lane 4; FIG. 13C) was protected from bases 11–21), with absolute protection of bases 14–19. The top strand DNA (FIG. 13B, lane 4; FIG. 13C) was protected for bases 12–24, with absolute protection of bases 13–21. This result shows that the 3' half of the element contains a protein binding site.

Protection of the upper band of wild-type element extended beyond the palindrome for at least two bases in either direction. In the lower band, protection extended at least two bases 5' of the palindrome sequence (FIG. 12C) and one base beyond the internal boundary of the half palindrome was partially protected. In the 3.3 element, where binding was restricted to the 3' half of the palindrome, protection again extended two to five bases beyond the palindrome boundary (FIG. 13C).

We claim:

1. A recombinant DNA molecule comprising a DNA fragment which fragment is a plant enhancer element capable of being bound by an OCS transcription factor and displaying the upper band binding pattern characteristic of the wild-type ocs enhancer in gel retardation assays, said fragment consisting essentially of a consensus sequence selected from the group consisting of

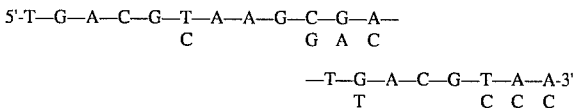

and its reverse sequence, in combination with (a) a plant-expressible promoter heterologous to said plant enhancer element wherein said promoter is placed 3' to said enhancer element, and (b) a plant-expressible structural gene wherein said gene is placed 3' to said promoter and under the regulatory control of said enhancer element and said plant-expressible promoter.

2. A recombinant DNA molecule of claim 1 wherein the enhancer element is located between the 5' end of the TATA box of said promoter and about 1500 bp 5' of the transcription initiation site of said plant-expressible gene.

3. The recombinant DNA molecule of claim 1 wherein said plant-expressible promoter and said plant-expressible gene are derived from an anaerobically regulated gene.

4. The recombinant DNA molecule of claim 1 wherein said promoter and said gene are derived from an alcohol dehydrogenase (adh) gene.

5. The recombinant DNA molecule of claim 1 wherein said promoter and said structural gene are derived from the adh1 gene of maize.

6. The recombinant DNA molecule of claim 1 wherein said promoter and said gene are derived from pea.

7. The recombinant DNA of claim 1 wherein said structural gene encodes a *Bacillus thuringiensis* insect toxin.

8. The recombinant DNA molecule of claim 1 wherein said enhancer element further comprises a second component, wherein said second component in said DNA molecule consists essentially of a sequence selected from the group consisting of 5'-GATGTTAACATC-3' and its reverse sequence, and wherein said second component is located 5' or 3' to the consensus sequence of claim 8, wherein said second component is located 5' to said plant-expressible promoter, and wherein said second component is located between about 1 and about 500 bp of said consensus sequence.

9. The recombinant DNA molecule of claim 8 wherein both said elements are derived from T-DNA.

10. A method for enhancing expression of a plant-expressible structural gene in a transformable plant cell, said method comprising inserting a DNA fragment which is a plant enhancer element of claim 1 into the genome of said plant cell such that said plant expressible structural gene is under regulatory control in said plant cell of said plant enhancer element and a promoter heterologous to said enhancer element.

11. The method of claim 10 wherein said DNA fragment also comprises a second component consisting essentially of a sequence selected from the group consisting of 5'-GATGTTAACATC-3' and its reverse sequence.

12. The method of claim 10 wherein said plant enhancer element is derived from T-DNA.

13. The method of claim 10 wherein said promoter and said structural gene are derived from an anaerobically regulated gene.

14. A recombinant DNA molecule of claim 1, wherein said fragment is selected from the group consisting of:

Ti OCS: 5' AAACGTAAGCGCTTACGTAC 3';
CaMV 35S: 5' TGACGTAAGGGATGACGCAC 3';
FMV: 5' TGACGAACGCAGTGACGACC 3';
CERV: 5' AGACGTCATGCATGACGTTT 3';
Ri MAS1': 5' TTACGTCATCGCTTACGCAT 3';
Ri MAS2': 5' ATGCGTAAGCGATGACGTAA 3';
Ti MAS1': 5' TGACTCGGATACTTACGTCA 3';
Ti MAS2': 5' TGACGCTCGCGGTGACGCCA 3';
Ti NOS: 5' TGAGCTAAGCACATACGTCA 3'; and
Ti AGS: 5' TGACGCATCGAATGACGCGA 3'.

15. The method of claim 10, wherein said plant enhancer element is selected from the group consisting of:

Ti OCS: 5' AAACGTAAGCGCTTACGTAC 3';
CaMV 35S: 5' TGACGTAAGGGATGACGCAC 3';
FMV: 5' TGACGAACGCAGTGACGACC 3';
CERV: 5' AGACGTCATGCATGACGTTT 3';
Ri MAS1': 5' TTACGTCATCGCTTACGCAT 3';
Ri MAS2': 5' ATGCGTAAGCGATGACGTAA 3';
Ti MAS1': 5' TGACTCGGATACTTACGTCA 3';
Ti MAS2': 5' TGACGCTCGCGGTGACGCCA 3';
Ti NOS: 5' TGAGCTAAGCACATACGTCA 3'; and
Ti AGS: 5' TGACGCATCGAATGACGCGA 3'.

16. A recombinant DNA molecule comprising a DNA fragment which fragment is a plant enhancer element capable of being bound by an OCS transcription factor and displaying the upper band binding pattern characteristic of the wild-type ocs enhancer in gel retardation assays, wherein said fragment comprises the sequence 5'-ACGTAAGCGCTTACGT-3' and its reverse sequence, in combination with (a) a plant-expressible promoter heterologous to said plant enhancer element wherein said promoter is placed 3' to said enhancer element, and (b) a plant-expressible structural gene wherein said gene is placed 3' to said promoter and under the regulatory control of said enhancer element and said plant-expressible promoter.

17. A method for enhancing expression of a plant-expressible structural gene in a transformable plant cell, said method comprising inserting a DNA fragment which is a plant enhancer element of claim 16 into the genome of said plant cell such that said plant expressible structural gene is under regulatory control in said plant cell of said plant enhancer element and a promoter heterologous to said enhancer element.

* * * * *

UNITED STATES PATENT AND TRADEMARK OFFICE
CERTIFICATE OF CORRECTION

PATENT NO. : 5,573,932  
DATED : November 12, 1996  
INVENTOR(S) : Ellis *et al.*

Page 1 of 3

It is certified that error appears in the above-indentified patent and that said Letters Patent is hereby corrected as shown below:

Column 2, line 62: "CaMVis" should read --CaMV is--

Column 5, line 2: "pti15559" should read --pTi 15559--

Column 9, line 15: "TDNAs" should read --T-DNAs-- line 52: "a.cloned" should read --a cloned-- line 54: "the Binding" should read --the binding--

Column 10, line 20: "-295.ags construct" should read --295 ags construct--

Column 12, line 63: "ocs transcriptional" should read -ocs transcription-line 65: "ocs transcriptional" should read --ocs transcription-- line 66: "OCS element" should read --ocs element-- line 67: "ocs Transcriptional" should read --ocs transcription--

Column 15, line 30: "of the ocs. promoter" should read --of the ocs promoter--

Column 16, line 44: "to the OSC nuclear" should read --to the ocs nuclear-- line 59: "to CaMVand" should read --to CaMV and--

UNITED STATES PATENT AND TRADEMARK OFFICE
CERTIFICATE OF CORRECTION

PATENT NO. : 5,573,932

DATED : November 12, 1996

INVENTOR(S) : Ellis *et al.*

It is certified that error appears in the above-indentified patent and that said Letters Patent is hereby corrected as shown below:

Column 18, line 22: "TagI site" should read --TaqI site--

Column 21, line 17: "(5'-AA-TGTGA-T----C-3')" should read

--(5'-AA-TGTGA--T----C-3')--

Column 23, line 48: "plasmid pad2." should read --plasmid pAd2.-- line 56: "the TagI" should read --the TaqI-- line 59: "into pad2 cut" should read --into pAd2 cut--

Column 24, line 4: "pad2." should read --pAd2.--; line 4: "TagI" should read --TaqI-- lines 9&10: "EMBO J. 277-284)" should read --EMBO J. $\underline{4}$:277-284)--

Column 25, line-27: "250 µl 10.25 Tris-Cl," should read --250 µl 0.25 Tris-Cl,--

Column 29, line 33: "nuclear .extract" should read --nuclear extract--

Column 31, line 2: "of theMAS promoters" should read --of the MAS promoters--

UNITED STATES PATENT AND TRADEMARK OFFICE
CERTIFICATE OF CORRECTION

PATENT NO. : 5,573,932
DATED : November 12, 1996
INVENTOR(S) : Ellis *et al.*

It is certified that error appears in the above-indentified patent and that said Letters Patent is hereby corrected as shown below:

Column 33, line 48: "to TagI of" should read --to TaqI of--

Column 34, line 7: "of the nos. promoter" should read --of the nos promoter.--

Column 35, line 39: "11:141-1158)." should read --11:141-158).--

Column 40, line 4: "regulatory control in said plant cell" should read --regulatory control --

Signed and Sealed this

Twenty-fifth Day of November, 1997

Attest:

BRUCE LEHMAN

*Attesting Officer*   *Commissioner of Patents and Trademarks*